US006861431B2

(12) United States Patent
Gudkov et al.

(10) Patent No.: US 6,861,431 B2
(45) Date of Patent: Mar. 1, 2005

(54) COMPOUNDS CAPABLE OF MODULATING THE ACTIVITY OF MULTIDRUG TRANSPORTERS AND THERAPEUTIC USE OF THE SAME

(75) Inventors: Andrei Gudkov, Gates Mills, OH (US); Roman Kondratov, Highland Heights, OH (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 50 days.

(21) Appl. No.: 10/104,604

(22) Filed: Mar. 22, 2002

(65) Prior Publication Data

US 2003/0073611 A1 Apr. 17, 2003

Related U.S. Application Data

(60) Provisional application No. 60/278,218, filed on Mar. 23, 2001, and provisional application No. 60/300,023, filed on Jun. 21, 2001.

(51) Int. Cl.$^7$ .............................................. A61K 31/50
(52) U.S. Cl. .................... 514/252.1; 514/403; 514/359; 514/260; 514/293; 514/374; 514/256; 514/264; 514/267; 514/383; 514/367
(58) Field of Search .............................. 514/252.1, 403, 514/359, 260, 293, 374, 256, 264, 267, 383, 367, 366

(56) References Cited

U.S. PATENT DOCUMENTS

| 5,403,574 | A | 4/1995 | Piwnica-Worms |
| 6,025,473 | A | 2/2000 | Deeley et al. |
| 2002/0037843 | A1 * | 3/2002 | Reiner et al. .................. 514/11 |
| 2002/0128264 | A1 * | 9/2002 | Taylor ..................... 514/228.2 |

FOREIGN PATENT DOCUMENTS

| WO | WO 99/39731 | 8/1999 |
| WO | WO 00/44364 | 8/2000 |
| WO | WO 00/46347 | 8/2000 |
| WO | WO 01/80896 | 11/2001 |
| WO | WO 02/14321 | 2/2002 |

OTHER PUBLICATIONS

M.M. Gottesman et al., *Annu. Rev. Biochem.*, 62, pp. 385–427 (1993).
B. Tan et al., *Curr. Opin. Oncol.*, 125, pp.50–58 (2000).
A.H. Schinkel et al., *Cell*, 77, pp. 491–502 (1994).
A. Lorico et al., *Cancer Res.*, 57, pp. 5238–5242 (1997).
J.J. Smit et al., *Cell*, 75, pp. 451–462 (1993).
K.H. Choi et al., *Cell*, 53, pp. 519–529 (1988).
S. Kajiji et al., *Biochemistry*, 32, pp. 4185–4194 (1993).
C.A. Hrycyna et al., *Methods Enzymol.*, 292, pp. 456–473 (1998).
R.S. Gupta, *Biochem. Biophys. Res. Commun.*, 153, pp.598–605 (1988).
S. Akiyama et al., *Somat. Cell. Mol. Genet.*, 11, pp. 117–126 (1985).
J.M. Phang et al., *Cancer Res.*, 53, pp. 5977–5981 (1993).
J.M. Critchfield et al., *Biochem. Pharmacol.*, 48, pp. 1437–1445 (1994).
G. Scambia et al., *Cancer Chemother. Pharmacol.*, 34, pp. 459–464 (1994).
J. Ferte et al., *J. Med. Chem.*, 42, pp. 478–489 (1999).
D.F. Robbiani et al., *Cell*, 103, pp. 757–768 (2000).
P.G. Komarov et al., *Science*, 285, pp. 1733–1737 (1999).
P. Borst, *Seminars in Cancer Biology*, 8, pp. 131–134 (1997).
J. Konig et al., *BBA*, 1461, pp. 377–394 (1999).
B. Sarkadi et al., *Seminars in Cancer Biology*, 8, pp. 171–182 (1997).
A. Schinkel, *Seminars in Cancer Biology*, 8, pp. 161–170 (1997).
A.H. Schinkel et al., *Proc. Natl. Acad. Sci. USA*, 94, pp. 4028–4033 (1997).
P. Gros et al., *Proc. Natl. Acad. Sci. USA*, 88, pp. 7289–7293 (1991).
A.R. Safa et al., *Proc. Natl. Acad. Sci. USA*, 87, pp. 7225–7229 (1990).
E.B. Mechetner et al., *Proc. Natl. Acad. Sci. USA*, 94, pp. 12908–12913 (1997).
A.B. Shapiro et al., *Eur. J. Biochem.*, 259, pp. 841–850 (1999).
S.L. Bogza et al., *J. Heterocyclic Chem.*, 38, 523 (2001).
A. Singh et al., *Indian J. Chem.*, vol. 14B, No. 12, 997–998 (1976).
M.N. Balse et al., *Indian Journal of Chemistry*, vol. 19B, 263–265 (1980).
U. Heinz et al., *Zeitschrift Fuer Kristallographie*, vol. 216, No. 1, 113–114 (2001).
R.V. Kondratov et al., Proceedings of the National Academy of Sciences of the United States of America, vol. 98, No. 24, 14078–14083 (2001).

* cited by examiner

Primary Examiner—James H Reamer
(74) Attorney, Agent, or Firm—Marshall, Gerstein & Borun LLP

(57) ABSTRACT

Methods of modulating the activity of multidrug transporters are disclosed. The methods of modulating the activity of multidrug transporters use compounds that selectively increase or decrease the efflux capabilities of the multidrug transporter. The methods can be used therapeutically to enhance performance of therapeutic drugs, like chemotherapeutic drugs and antibiotics; to promote detoxification of cells and tissues; and to increase or decrease the efficacy of the blood-brain barrier or placental barrier.

12 Claims, 16 Drawing Sheets

COMPOUNDS CAPABLE OF MODULATING THE ACTIVITY OF MULTIDRUG TRANSPORTERS AND THERAPEUTIC USE OF THE SAME

CROSS REFERENCE TO RELATED APPLICATION

This application claims the benefit of U.S. provisional Patent Application No. 60/278,218, filed Mar. 23, 2001, and U.S. provisional Patent Application No. 60/300,023, filed Jun. 21, 2001.

FIELD OF THE INVENTION

The present invention relates to compounds capable of modulating the activity of multidrug transporters, and their use in therapy, for example, in cancer treatment, in modulating efficacy of a blood-brain barrier or placental barrier, and in facilitating detoxification of a cell or tissue. More particularly, the present invention relates to compounds having the ability to effectively modulate the efflux capability of a multidrug transporter, and that can be used therapeutically, alone or in conjunction with a therapy, like chemotherapy or radiation therapy during cancer treatment, in a method to treat a disease or condition wherein modulation of multidrug transporter activity provides a benefit. The present invention is directed both to compounds that promote, and compounds that inhibit, the efflux capability of a multidrug transporter, wherein transporter activity through gene expression is unaffected.

BACKGROUND OF THE INVENTION

P-glycoprotein (P-gp) belongs to a superfamily of ABC transporters found both in pro- and eucaryotes that act as energy-dependent efflux pumps for transporting a wide variety of low molecular weight compounds out of cells (for a review see reference 1 of Appendix A). ABC transporters are a constantly growing superfamily of membrane proteins found in bacteria through humans. ABC transporters use energy of ATP hydrolysis for transport of a wide spectrum of compounds (e.g., anticancer drugs, toxins, antibiotics, and lipids) from cells. In mammals, this superfamily includes, in addition to the P-gp transporters (MDR1 and MDR3 in humans), the MRP subfamily (already including 6 members), and several other proteins (e.g., LRP and BCRP) (2,3).

The majority of ABC transporters have an ability to recognize and efflux numerous substrates of divergent chemical structure, including many anticancer drugs, from cells and tissue. The molecular mechanisms underlying broad substrate specificity of ABC transporters are generally unknown (3). The expression of ABC transporters results in cross resistance of cells to numerous toxic compounds, known as multidrug resistance (MDR) (1,3,4).

Increased expression of ABC transporters in tumor cells is one of the major mechanisms of cancer resistance to chemotherapy (1–3). Although the clinical relevance of multidrug resistance is debated, P-gp and other ABC transporters are viewed as targets for therapeutic suppression to increase the susceptibility of multidrug resistant cancers to chemotherapy (5).

The understanding of the normal physiological role of ABC transporters is derived from an analysis of phenotypes of mice genetically deficient in the genes encoding these proteins. Mice lacking both mdr1a and mdr1b genes (i.e., two homologs of human P-gp-encoding MDR1 gene with different tissue expression (6)) develop normally, but were found to be extremely sensitive to particular xenobiotics and have strong alterations in pharmacokinetics of drugs known to be P-gp substrates (7,8). Moreover, a deficiency in P-gp was associated with the ability of P-gp substrates to pass through blood-brain barrier (6,7,8).

In mammals, and particularly in humans, the expression of ABC transporters is restricted to specific organs, including the intestine, kidney, liver, endothelia of brain, testis, and placenta, which is consistent with role of these organs in general detoxification and in establishment of blood-brain, blood-testis, and placental barriers (6). Although no physiological abnormalities were observed in the mice deficient in mpr1 gene, the mice did demonstrate increased sensitivity to particular toxins and changes in glutathione metabolism (9). Robbiani et al. also reported possible involvement of MRP1 in dendritic cells migration to lymph nodes (10).

Some members of the superfamily of ABC transporters apparently have a more narrow and specific spectrum of substrates, e.g., targeted disruption of mdr2 gene in mice results in a deviation in phosphatidylcholine and other phospholipid excretion in a bile (11). Thus, in addition to an ABC supertransporter role in cancer resistance to chemotherapy, ABC transporters are involved in numerous physiological processes and their value as therapeutic targets is envisioned as far broader than cancer treatment.

Over the last several years, chemical and protein inhibitors of ABC transporters have been developed to overcome MDR, and many of the inhibitors have been tested in clinical trials. However, there is a need not only for inhibitors of ABC transporters, but also for inducers of their activity and modulators of their substrate specificity. This need stems from the natural function of these proteins, which is known to be involved in protection of cells and tissues of an organism from cytotoxic compounds. Thus, compounds having such modulating properties can be used to facilitate detoxification of cells and tissues under conditions of acute or chronic poisoning.

It was previously found (5) that mutations of P-gp, the best studied ABC transporter, can strongly alter substrate specificity, thereby changing the pattern of cross resistance of cells expressing mutant P-gp, presumably by changing protein conformation. The present invention is directed to a similar effect caused by compounds capable of modulating multidrug transporting activity or modulating substrate specificity of multidrug transporters.

SUMMARY OF THE INVENTION

The present invention is directed to modulation of ABC transporter activity and substrate specificity in therapeutic applications. The present invention also is directed to compounds that effectively modulate ABC transporter activity and substrate specificity, and to the therapeutic use of such compounds.

Therefore, one aspect of the present invention is to provide a method of modulating the efflux capability of an ABC transporter in a cell or tissue by contacting the cell or tissue with a compound that promotes or inhibits efflux attributed to the ABC transporter, wherein activity of the ABC transporter through gene expression is unaffected.

Another aspect of the present invention is to provide a method of potentiating the activity of a therapeutic drug in a cell or tissue by contacting the cell or tissue with a compound that activates or inhibits the efflux capability of an ABC transporter, wherein activity of the ABC transporter through gene expression is unaffected.

In particular, the efflux capability of the ABC transporter can be selectively inhibited to retain a therapeutic drug, like a chemotherapeutic drug or antibiotic drug in the cell, while maintaining normal efflux capabilities with respect to other compounds.

Conversely, the efflux capability of the ABC transporter can be selectively activated to maintain normal efflux capabilities with respect to all compounds except a therapeutic drug, like a chemotherapeutic drug.

Yet another aspect of the present invention is to provide a method of facilitating detoxification of a cell or tissue by contacting the cell or tissue with a compound that increases the efflux capability of an ABC transporter, wherein activity of the ABC transporter through gene expression is unaffected. In particular, the efflux capability of the ABC transporter is selectively increased with respect to eliminating a predetermined toxin, e.g., a carcinogen, while maintaining normal efflux capabilities with respect to other compounds in the cell.

Still another aspect of the present invention is to provide a method of modulating the efficacy of a blood-brain barrier or placental barrier comprising administering to an individual in need thereof a therapeutically effective amount of a compound capable of modulating the activity of an ABC transporter, wherein activity of the ABC transporter through gene expression is unaffected.

In one embodiment, the efficacy of the blood-brain barrier or placental barrier is reduced. In this embodiment, barrier efficacy is selectively reduced with respect to a predetermined compound, e.g., a therapeutic drug, while maintaining normal barrier efficacy with respect to other compounds. In another embodiment, the efficacy of the blood-brain or placental barrier is increased. In this embodiment, barrier efficacy is selectively increased with respect to a predetermined compound, e.g., an acute or chronic toxin, while maintaining normal efflux efficacy with respect to other compounds.

Still another aspect of the present invention is to provide an improved composition for treating a disease or condition comprising:

(a) a therapeutic drug useful in the treatment of the disease or condition, and (b) a compound capable of selectively inhibiting the efflux capability of a multidrug transporter with respect to the therapeutic drug. For example, the disease or condition is a cancer or an infection, and the therapeutic drug is a chemotherapeutic drug or an antibiotic, respectively.

As used herein, an "infection" is defined as a bacterial, viral, parasitic, or other microbiological infection, and diseases and conditions resulting therefrom.

Another aspect of the present invention is to provide a pharmaceutical composition comprising (a) a compound capable of modulating the activity of a multidrug transporter, and (b) a pharmaceutically acceptable carrier.

These and other aspects of the present invention will become apparent from the following nonlimiting, detailed description of the preferred embodiments.

DETAILED DESCRIPTION OF THE PREFERRED EMBODIMENTS

Figure 1:
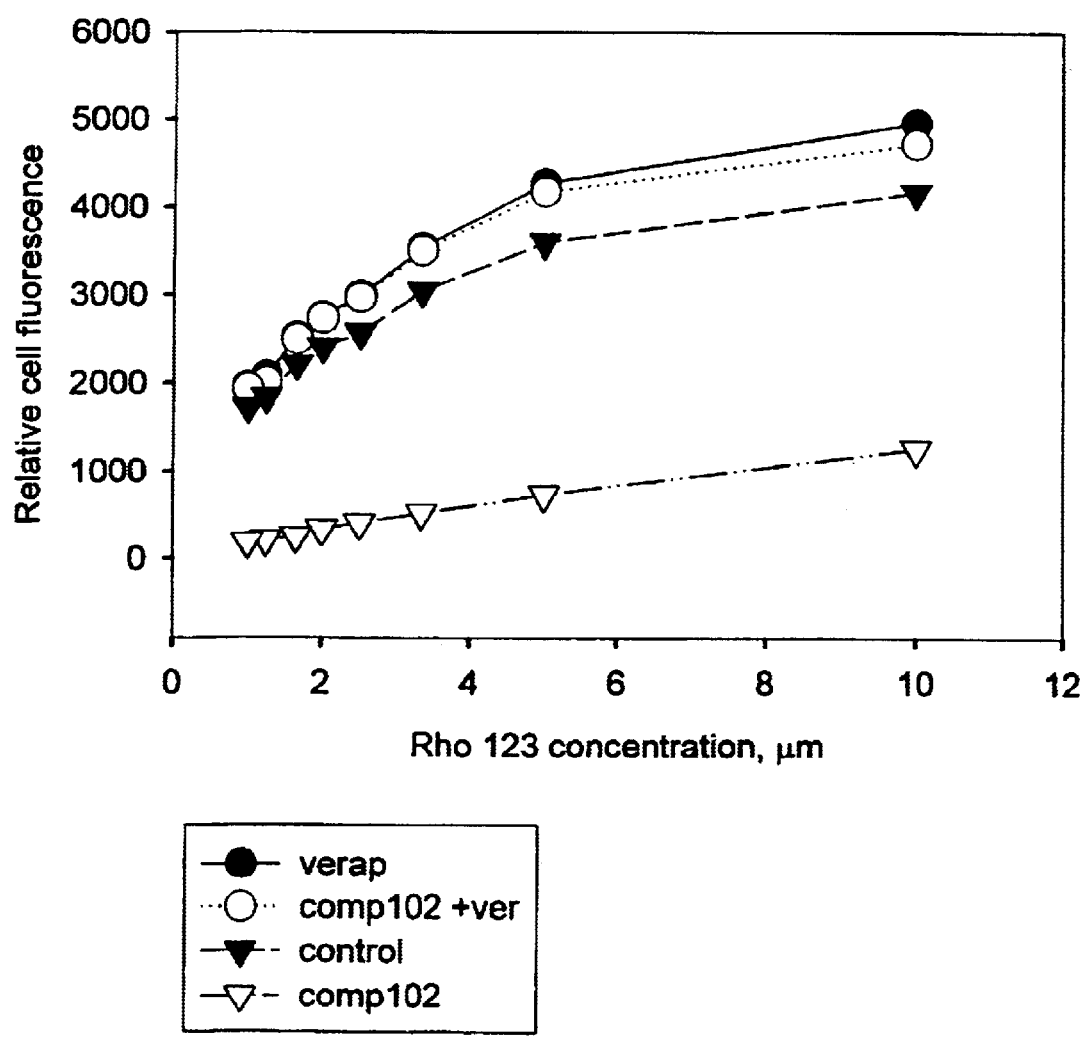
FIG. 1 contains plots of relative cell fluorescence vs. Rho123 concentration ($\mu$M) for tests to determine Rho123 accumulation.

Screening of chemical libraries for compounds that are biologically active at particular cellular targets is useful both as a research tool and for identification of therapeutic agents (12). Because ABC transporters traditionally are viewed as targets for therapeutic suppression, a number of small molecule and protein inhibitors of ABC transporters were developed during last decade, some of which have been tested in clinical trials to overcome MDR (5).

In accordance with the present invention, another potential therapeutic value of ABC transporters was investigated. In particular, ABC transporters were considered as targets for activation in order to increase their protective role against a variety of toxins.

It was previously shown that P-gp activity against particular substrates could be significantly modulated by specific mutations presumably affecting conformation of drug-recognizing domains of the protein (13, 14, 15, 16). The present invention is directed to small molecules that modify conformation of the transporter and have similar effect on transporter activity.

Such compounds can be identified by screening compounds that protect P-gp-expressing cells from the toxicity of certain P-gp substrates. As set forth hereafter, a series of compounds that protect P-gp-expressing cells from Adr by modulating substrate specificity of P-gp, which is associated with dramatic changes in the spectrum of cross-resistance, has been identified.

As used herein, the term "substrate" is defined as a compound that is effluxed from a cell by an ABC transporter.

The term "natural substrate" is defined as a substrate that is effluxed by the ABC transporter in the absence of compound that modulates transporter efflux capabilities.

Useful ABC transporter modulators were identified by screening a chemical library for compounds that protect P-gp-expressing cells from cytotoxic effects of P-gp substrates by stimulating their P-gp-mediated efflux. The results allowed identification of chemicals capable of inducing P-gp activity against particular substrates. Testing of the effects of an identified compound on cell sensitivity to a large variety of P-gp substrates, including many chemotherapeutic drugs, showed that they did not act as general activators of transporter function, but as modulators that more effectively efflux some P-gp substrates and render P-gp efflux less effective against other substrates.

Identified small molecules, differing in their effects on relative efficacy of P-gp against different substrates, form a new functional group of structurally divergent compounds defined as P-gp modulators, that are capable of modifying substrate specificity of P-gp. The compounds can be used for specifically targeting multidrug transporters against specific toxins. Because P-gp is representative of a group of structurally and functionally similar ABC transporters, the results and principles of identification disclosed herein can be extended to other members of this protein family, which results in the identification of modulators of cell sensitivity to a variety of toxic agents.

Materials and Methods

Drugs. Rhodamine 123 (Rho123), adriamycin (Adr), daunorubicin, taxol, etoposide, vinblastine, vincristine, cytochalasin B, colcemid, colchicine, actinomycin D, gramicidin D, verapamil hydrochloride, prazosin, progesterone, puromycin, and Hoechst 33342 were purchased from Sigma, Milwaukee, Wis., and (except progesterone) were dissolved in DMSO at a concentration of 1 mM. Progesterone was dissolved in PBS (phosphate-buffered saline) at a concentration 1 mM.

Cells. Mouse fibroblast cell line ConA, human cell lines KB-3-1, and its drug resistant derivative KB-8-5-11 were maintained in DMEM with 10% FBS, 2 mM glutamine, 100 u/ml penicillin G, 100 g/ml streptomycin sulfate (all Gibco BRL). At every fourth passage, KB-8-5-11 were cultivated in the presence of 25 ng/ml of Adr to eliminate revertants with decreased expression of P-gp.

Screening of a chemical library. Murine fibroblastoid cell line (ConA) was selected as the readout system for screening a chemical library for P-gp activators. ConA was selected because of a relatively effective high natural level of P-gp expression associated with effective efflux of different P-gp substrates. Rho123, a classic fluorescent P-gp substrate that is detected easily using multichannel fluorimeter in living cells, was used as an efflux indicator. CHEMICAL DIVERSET™ library was purchased from Chembridge Corp. (San Diego, Calif.). Primary screening was performed on ConA cells for compounds that interfere with Adr-induced activation of p53-responsive reporter LacZ gene as previously described (11). To identify P-gp modulators, all "hits" isolated after primary screening were tested for their ability to modulate cellular accumulation of Rho123. Con A cells grown in 96-well plates were incubated 4 hours with 0.5 $\mu$M Rho123 in combination with individual library compounds (2 $\mu$g/ml (2–5 $\mu$M)), and cell fluorescence was analyzed using fluorescent microscopy.

Drug sensitivity assays. To estimate drug-mediated growth inhibition, $10^3$ cells were plated per well of 96-well plates, and incubated with a range of concentrations of drugs added 24 hours after plating. After 5 to 7 hours of drug treatment, plates were fixed and stained using 2% methylene blue solution in 50% methanol. After elution by 1% SDS solution, optical density was determined on a Multiscan Ascent reader (Lybsystems, Helsinki, Finland) at 650 nm.

Drug accumulation and efflux assay. To determine drug accumulation, cells were incubated for two hours with P-gp substrates Rho123, Hoechst 33342, daunorubicin, or $^3$H-taxol (NEB) harvested by trypsinization, suspended in ice-cold PBS for immediate flow cytometric analysis (for fluorescent substrates) or scintillation counting of incorporated radioactivity (for $^3$H-taxol). For drug efflux assay, cells after drug incubation were washed thoroughly with PBS, incubated in a drug-free media with or without compounds from the chemical library, and harvested at different time points for flow cytometric analysis (18).

Western blot analysis. KB-8-5-11 and KB-3-1 cells were incubated for four hours with selected compounds, and the amounts of P-gp were estimated using Western blotting with monoclonal antibody C219 (Signet Corp., Dedham, Mass.) as previously described (17).

Determination of cell surface expression of P-gp and UIC2 shift assay were performed using monoclonal antibodies C219 and UIC2 as described in (18).

Flexible alignment of 3D structures was performed using software MOE-Flexalign, MOE 2001.0, available from Chemical Computing Group Inc., Montreal, Canada.

Results

Compounds that Suppress Cell Sensitivity to Adr in a p53-independent Manner

Treatment of cells with Adr results in the activation of the p53 pathway followed by modulated expression of p53-responsive genes. Therefore, cells expressing p53-responsive reporter can be used as a readout system for monitoring of Adr activity and screening of chemicals that interfere with p53-mediated activation of the reporter. Such a readout system for screening a chemical library for the compounds suppressing p53 has been successfully used previously (12). In order to demonstrate that the identified compounds act through p53 suppression, the initial "hits" were subjected to additional filtering for their p53 dependence.

In addition to p53 inhibitors, a group of chemicals that prevent activation of p53-responsive reporter by Adr in p53-independent manner were identified. Because Adr is a known substrate for ABC-type transporters, the potential involvement of active efflux in the biological effect of the identified compounds by introducing additional screening filters was investigated. First, it was found that these compounds interfered with the accumulation of Adr in the cells as determined by fluorescent microscopy. Similarly, the compounds reduced accumulation of another substrate of P-gp, i.e., Rho123 (see FIG. 1).

Figure 2:
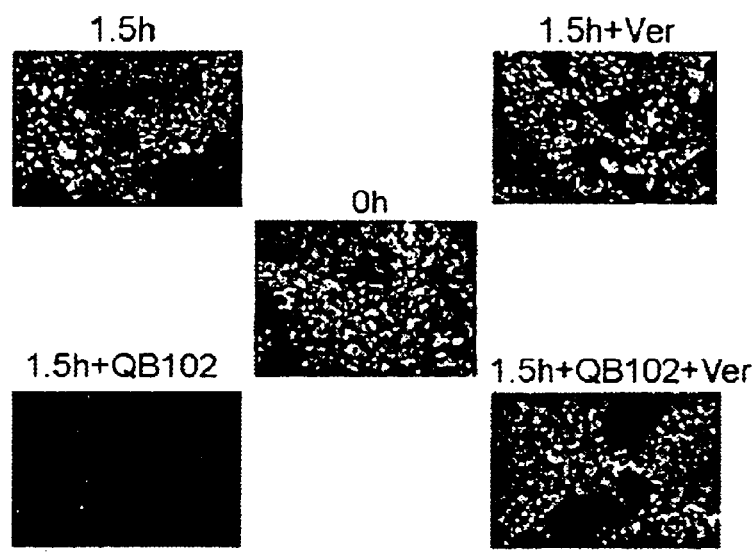
FIG. 2 contains results of fluorescence microscopy for the intensity of cellular fluorescence.
Figure 3:
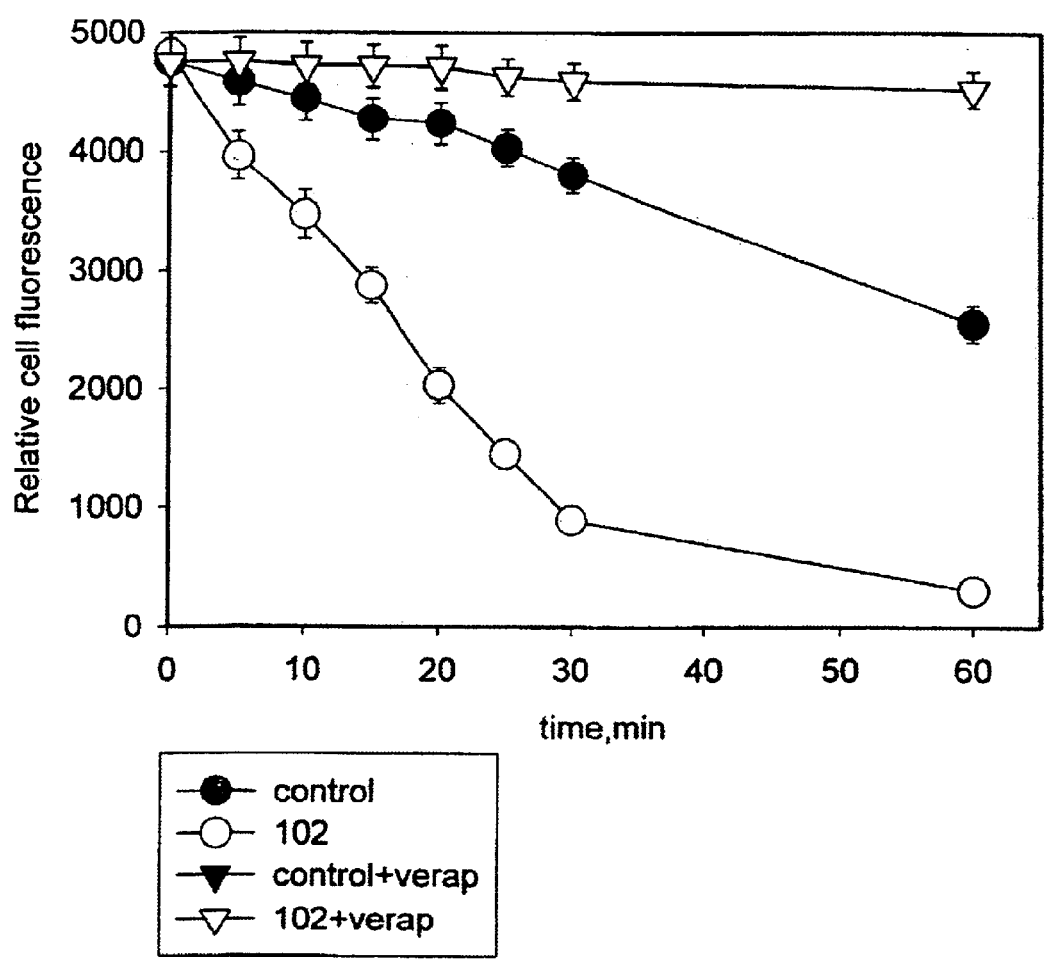
FIG. 3 contains plots of relative cell fluorescence vs. time (min.) for tests to determine Rho123 efflux.

FIGS. 1–3 show stimulation of Rho123 efflux from the cells by Compound 102 is suppressed by the P-gp inhibitor verapamil. In FIG. 1, Compound 102-mediated reduction of Rho123 accumulation by ConA fibroblasts is suppressed by verapamil. Cells were incubated two hours with the indicated concentrations of Rho123, Compound 102, and verapamil, and cellular fluorescence was analyzed by flow cytometry. Both effects were completely reverted by verapamil and reserpine, known inhibitors of P-gp. These results strongly indicate that the identified compounds acted by an unusual mechanism, i.e., through activation of P-gp or other ABC transporter sensitive to P-gp inhibitors. The structural formulas of thirteen compounds possessing the described properties are shown in Table 1.

TABLE 1
| Compound No. | Name | Structure |
|---|---|---|
| 2 | 1-Carbazol-9-yl-3-(3,5-dimethyl-pyrazol-1-yl)-propan-2-ol | 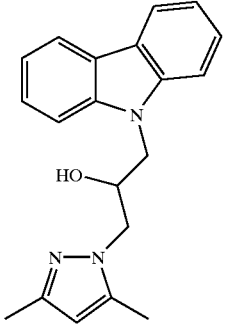 |
| 7 | 2-(4-Chloro-3,5-dimethyl-phenoxy)-N-(2-phenyl-2H-benzotriazol-5-yl)-acetamide | 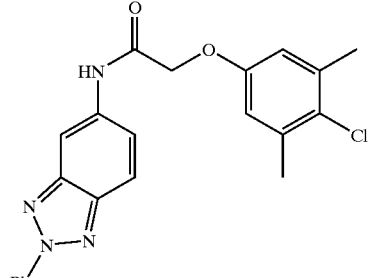 |
| 8 | N-[2-(4-Chloro-phenyl)-acetyl]-N'-(4,7-dimethyl-quinazolin-2-yl)-guanidine | 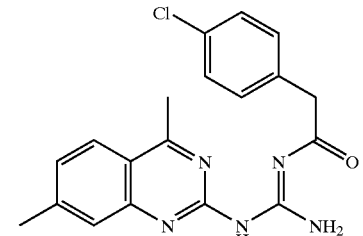 |
| 9 | 1-Benzyl-7,8-dimethoxy-3-phenyl-3H-pyrazolo[3,4-c]isoquinoline | 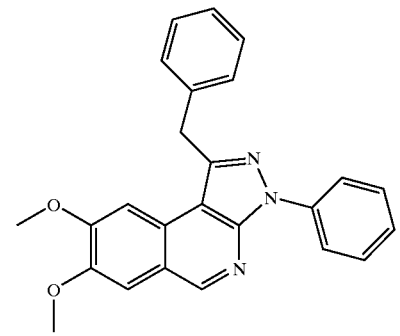 |
| 10 | N-(3-Benzooxazol-2-yl-4-hydroxy-phenyl)-2-p-tolyloxy-acetamide | 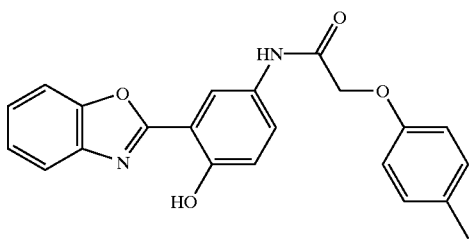 |

TABLE 1-continued

| Compound No. | Name | Structure |
|---|---|---|
| 11 | 8-Allyl-2-phenyl-8H-1,3a,8-triaza-cyclopenta[a]indene | 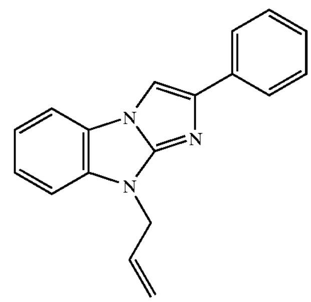 |
| 12 | 3-(4-Chloro-benzyl)-5-(2-methoxy-phenyl)-[1,2,4]oxadiazole | 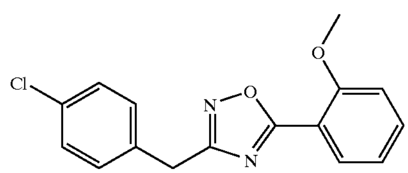 |
| 13 | 2-Phenethylsulfanyl-5,6,7,8-tetrahydro-benzo[4,5]thieno[2,3-d]pyrimidin-4-ylamine | 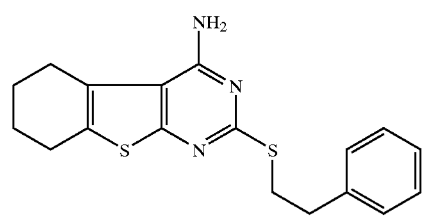 |
| 14 | (5,12,13-Triaza-indeno[1,2-b]anthracen-13-yl)-acetic acid ethyl ester | 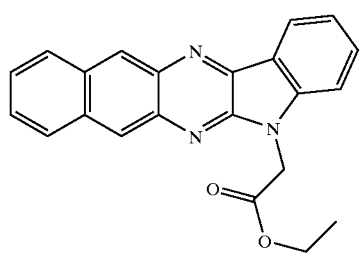 |
| 15 | 2,2'-(1-phenyl-1H-1,2,4-triazole-3,5-diyl)bis-phenol | 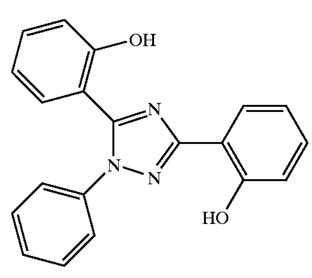 |
| 16 | 2-(2-Chloro-phenyl)-5-(5-methyl-thiophen-2-yl)-[1,3,4]oxadiazole | 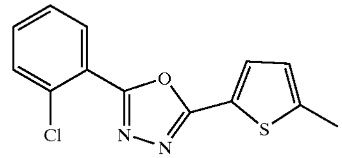 |

TABLE 1-continued

| Compound No. | Name | Structure |
|---|---|---|
| 102 | 2-p-Tolyl-5,6,7,8-tetrahydro-benzo[d]imidazo[2,1-b]thiazole | 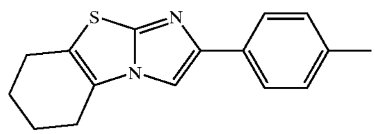 |
| 103 | | 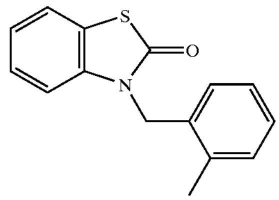 |

Identified Compounds Can Activate Efflux of Adr and Rho123 by P-gp

One of the most active compounds, designated Compound 102, was chosen for a detailed characterization. First, Compound 102 did not effect the excitation and emission spectra of Rho123 and Adr fluorescence in solution, thus eliminating the possibility of its direct effect on the physicochemical characteristics of the drugs.

A test for whether Compound 102 effects the accumulation of fluorescent dyes by stimulating efflux or by interfering with their penetration through the cell membrane was performed. Cells were loaded with Rho123 by incubation in the medium with high concentration of the dye (1M), quickly washed with the Rho123-free medium, and the dynamics of reduction of cellular fluorescence was monitored at different times in the presence or in the absence of Compound 102. The results (FIGS. 2 and 3) demonstrate that Compound 102 strongly increases (i.e., about 20 times) efflux of Rho123 from the cells preloaded with the dye. This effect was completely reverted by verapamil and reserpine. In the presence of these P-gp inhibitors, efflux of Rho123 was blocked regardless of the presence of Compound 102 (FIGS. 2 and 3).

In FIG. 2, cells were loaded with Rho123 by incubation in the presence of 1M of the dye, quickly washed with the Rho123-free medium and the intensity of cellular fluorescence was determined 1.5 hours later, either in the presence or in the absence of Compound 102 and verapamil by fluorescent microscope. FIG. 3 shows that Compound 102 stimulates Rho123 efflux by ConA cells. The dynamics of reduction of Rho123 fluorescence was monitored by flow cytometry. These observations demonstrate that Compound 102 acts by activating ABC transporters, presumably P-gp that is expressed in mouse fibroblasts (19).

To test the effect of Compound 102 specifically on P-gp, a pair of human cell lines used as conventional models for studying P-gp, i.e., P-gp-negative KB-3-1 and its multidrug resistant derivative KB-8-5-11, overexpressing P-gp as a result of MDR1 gene amplification (20), were used. Treatment with Compound 102 strongly decreased Rho123 accumulation in KB-8-5-11 cells and had no influence on KB-3-1 cells (FIG. 4).

Figure 4:
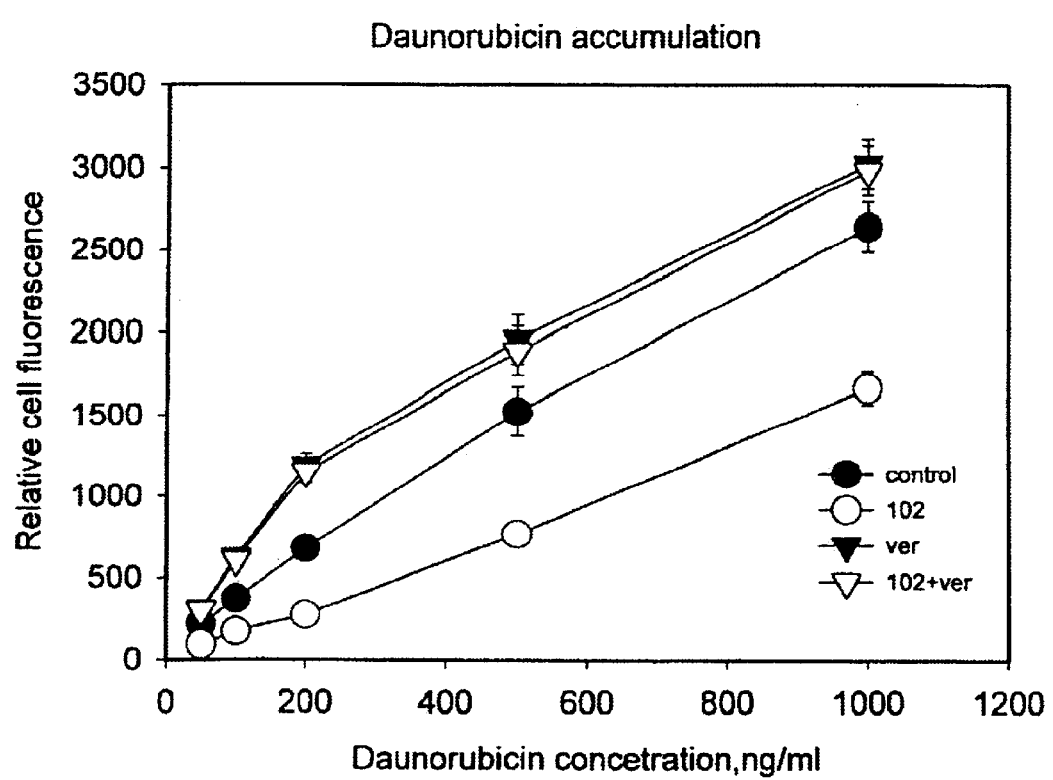
FIG. 4 contains plots of relative cell fluorescence vs. daunorubicin concentration (ng/ml) for tests to determine daunorubicin accumulation.
Figure 5:
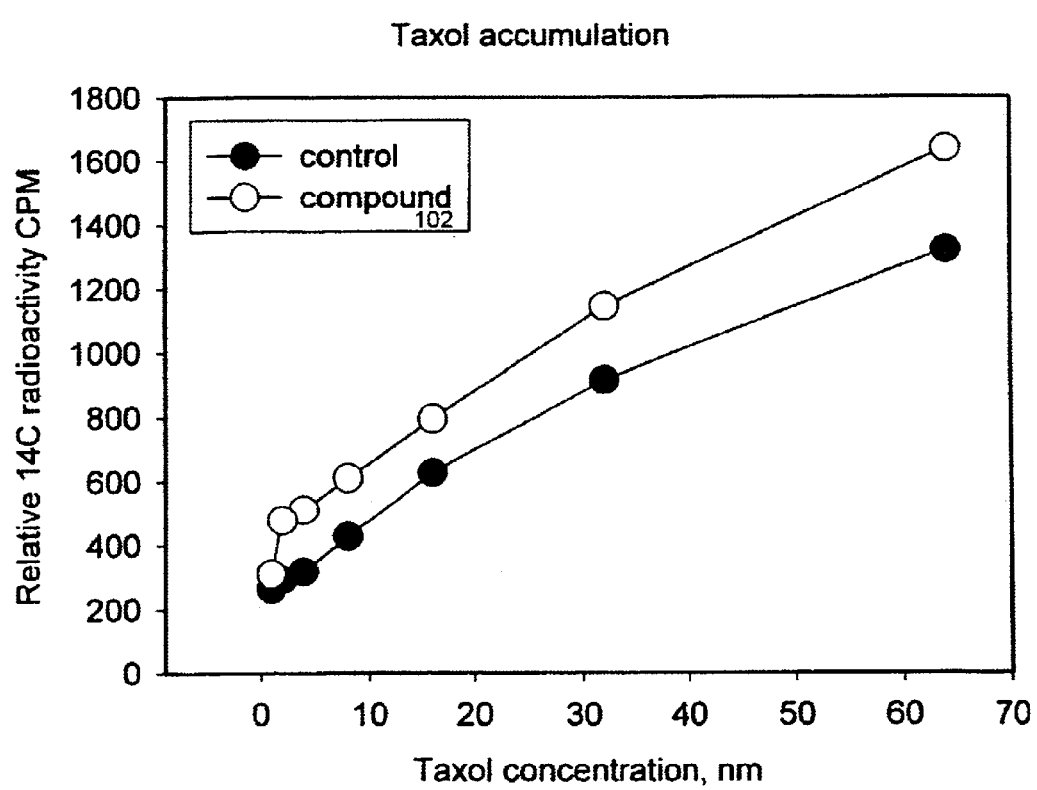
FIG. 5 contains plots of relative $^{14}$C radioactivity (CPM) vs. taxol concentration (nM) for tests to determine taxol accumulation.

FIGS. 4 and 5 show different effects of Compound 102 on cell accumulation and sensitivity to different P-gp substrates. As shown in FIGS. 4 and 5, Compound 102 has opposite effects on accumulation of daunorubicin and taxol. ConA cells were incubated 2 hours with the indicated concentration of daunorubicin (FIG. 4) and taxol (FIG. 5), and accumulation of the drugs was determined by flow cytometry (daunorubicin) or measurement of intracellular radioactivity ($^3$H-taxol). FIG. 5 shows that Compound 102 increases taxol accumulation by ConA cells.

To determine whether the effect of the identified compounds is similar for different P-gp substrates, their influence on the efflux of another well-known P-gp substrate, the chemotherapeutic drug taxol (paclitaxel), was tested. The results obtained with $^{14}$C-labeled paclitaxel (FIG. 5) indicate that accumulation of this drug was affected by the tested compounds in an opposite way than accumulation of daunorubicin or Rho123. This result shows that compounds identified for their stimulatory effect on P-gp against daunorubicin or Rho123, act not as general activators of the function of the transporter, but rather as modulators capable of more effective efflux of some of the P-gp substrates and making P-gp less effective against other substrates. Again, the decrease in accumulation correlated with stimulation of Rho123 efflux and both effects were completely eliminated by verapamil. Thus, Compound 102 definitely targets P-gp function, although it cannot be excluded that activity of other ABC transporters could also modulated by this compound.

The effect of Compound 102 on Rho123 efflux can be detected within five minutes after adding the compound (FIG. 3), leaving no time for gene expression to cause an effect. Four-hour incubation of KB-8-5-11 cells with Compound 102 did not change the amount of P-gp on the cell surface as determined by the results of FACS analysis with anti-P-gp antibodies UIC2. Accordingly, stimulation of P-gp function by Compound 102 cannot be attributed to changes in gene expression or protein concentration on cell membrane.

Compound 102 Alters Cellular Cross-resistance to Different Drugs by Modulating P-gp Function Whether activation of P-gp-mediated efflux of Adr by Compound 102 affects cell sensitivity using different types of drug assays also was tested. The results of representative growth inhibition assays are shown in FIG. 2. Compound 102 increased resistance to Adr in both murine ConA and human KB-8-5-11 cells causing a six-fold shift in 50% growth inhibitory dose of the drug in both cell lines (from 50 to 300 ng/ml and from 200 to 1200 ng/ml, respectively) (see FIGS. 4–7 and Table 2). No effect on drug sensitivity was detected in P-gp-negative cell line KB-3-1.

TABLE 2

Influence of Compound 102 on cellular effects of different drugs

| Increased resistance/efflux | Decreased resistance/efflux | No effect |
|---|---|---|
| Adriamycin | Taxol | Colcemide |
| Daunorubicin | Vinblastin* | Colchicine |
| Etoposide* | Vincristin* | Actinomycin D |
| Rhodamine 123** | Hoechst 33342** | Puromycin |
|  |  | Camptothecin*** |
|  |  | Carboplatin*** |
|  |  | 5-fluorouracil*** |

*only resistance was tested
**only efflux wax tested
***non-P-gp substrates

TABLE 3

| Drug | LD$_{50}$, ng/ml | LD$_{50\ comp}$, ng/ml | Change in sensitivity (x-fold) |
|---|---|---|---|
| Daunorubicin | 50 | 125 | 2.5 |
| Doxorubicin | 50 | 300 | 6 |
| Etoposide | 100 | 150 | 1.5 |
| Taxol | 200 | 70 | 0.3 |
| Vinblastine | 10 | 5 | 0.5 |
| Vincristine | 12.5 | 6 | 0.5 |
| Colchicine | 50 | 50 | 1 |
| Colcemide | 50 | 50 | 1 |
| Puromycin | 4 | 4 | 1 |
| Actinomicyn D | 20 | 20 | 1 |

Table 3 shows the effects of Compound 102 (10 μM) on sensitivity of ConA cells to different P-gp substrates (fold resistance).

Table 4 summarizes the effects of Compound 102 on sensitivity of P-gp-positive (ConA and KB-8-5-11) and P-gp-negative (KB-3-1) cells to different drugs (both P-gp substrates and non-P-gp-sub-strates). R—increases resistance; NE—no effect; S—sensitizing effect; n.d.—not done.

TABLE 4

Effect of Compound 102 on drug sensitivity of cell lines

| Drug | P-gp substrate | ConA (Balb 3T3) | KB-8-5-11 (HeLa, Pgp$^+$) | KB-3-1 (HeLa, Pgp*) |
|---|---|---|---|---|
| Doxorubicin* | Yes | R | R | NE |
| Daunorubicin* |  | R | R | NE |
| Rhodamine 123** |  | R | R | NE |
| Etoposide |  | Minor R | Minor R | NE |
| Puromycin |  | NE | NE | NE |
| Colcemide |  | NE | NE | NE |
| Cyclosporin A |  | NE | NE | NE |
| Actinomycin D |  | NE | NE | NE |
| Taxol |  | S | S | NE |
| Vincristine |  | S | S | NE |
| Gramicidine D |  | S | S | NE |
| Vinblastine |  | S | S | NE |
| Colchicine |  | S | S | NE |
| Hoechst 33342** |  | S? | S? | NE |
| 5-Fluorouracil | No | NE | NE | NE |
| Carboplatin |  | n.d. | NE | NE |
| Camptothecin |  | NE | NE | NE |

Figure 6:
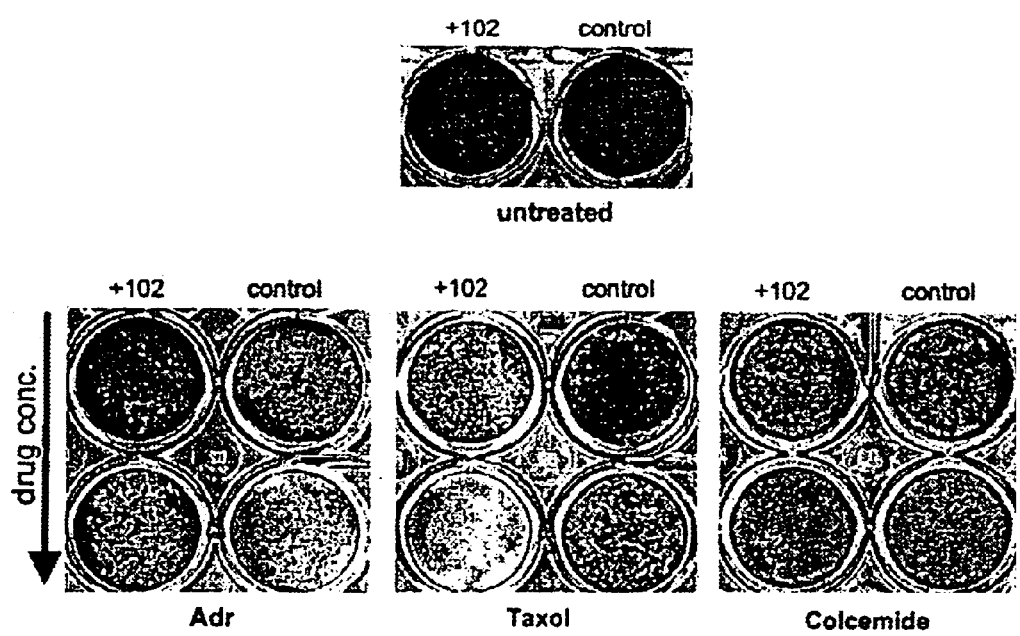
FIG. 6 contains photographs illustrating the effects of Compound 102 vs. Adr, taxol, and colcemide.
Figure 7:
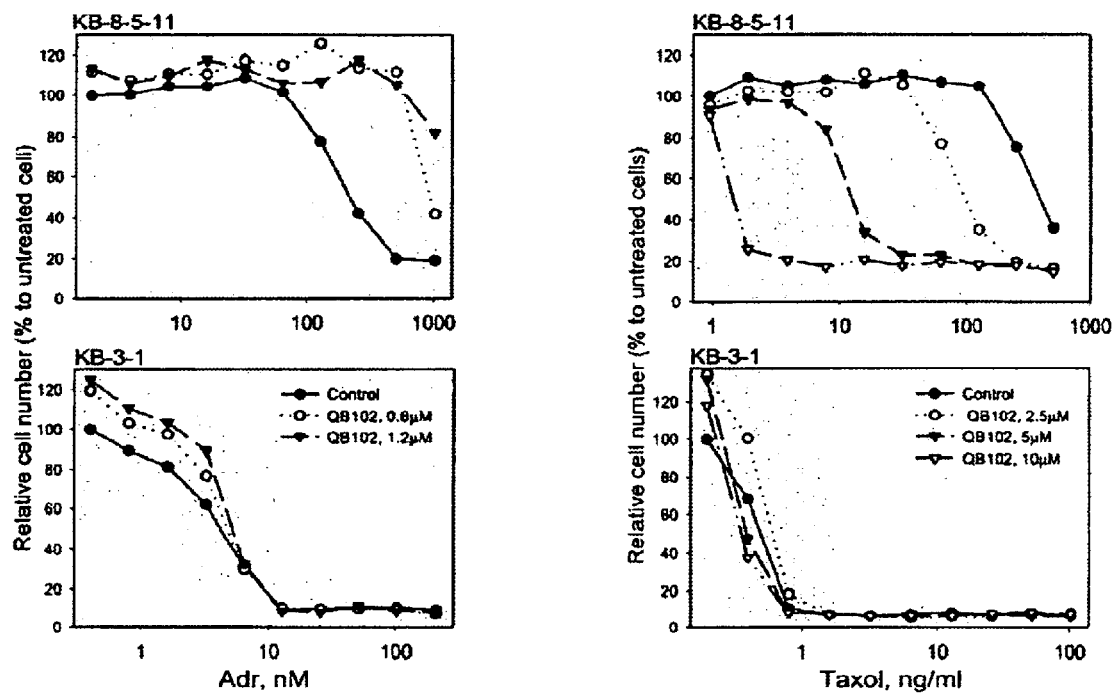
FIG. 7 contains graphs of Relative cell number (% of untreated cells) vs. Adr (nM) or taxol (ng/ml) for KB-8-5-11 and KB-3-1 cells.

FIG. 6 shows that Compound 102 has opposite effects on cytotoxicity of Adr and taxol, and does not affect cell sensitivity to colcemide. In particular, Compound 102 increases sensitivity to taxol, and decreases sensitivity to Adr. Compound 102 has no effect on cell sensitivity to colcemide, a non-P-gp substrate. ConA cells were grown 72 hours in presence different concentrations of indicated drugs with or without Compound 102, fixed with methanol and stained with methylene blue. FIG. 7 shows that the effect of Compound 102 on cell sensitivity to Adr and taxol is P-gp dependent. The results of colony assays performed P-gp positive (KB-8-5-11) and P-gp negative (KB-3-1) cells in constant presence of the indicated concentrations of the drugs. The effect of Compound 102 is dose dependent. This test demonstrated that the identified compounds act by modulating activity of the transporter, i.e., no compound showed any effect on P-gp-negative KB-3-1 cells.

Figure 10:
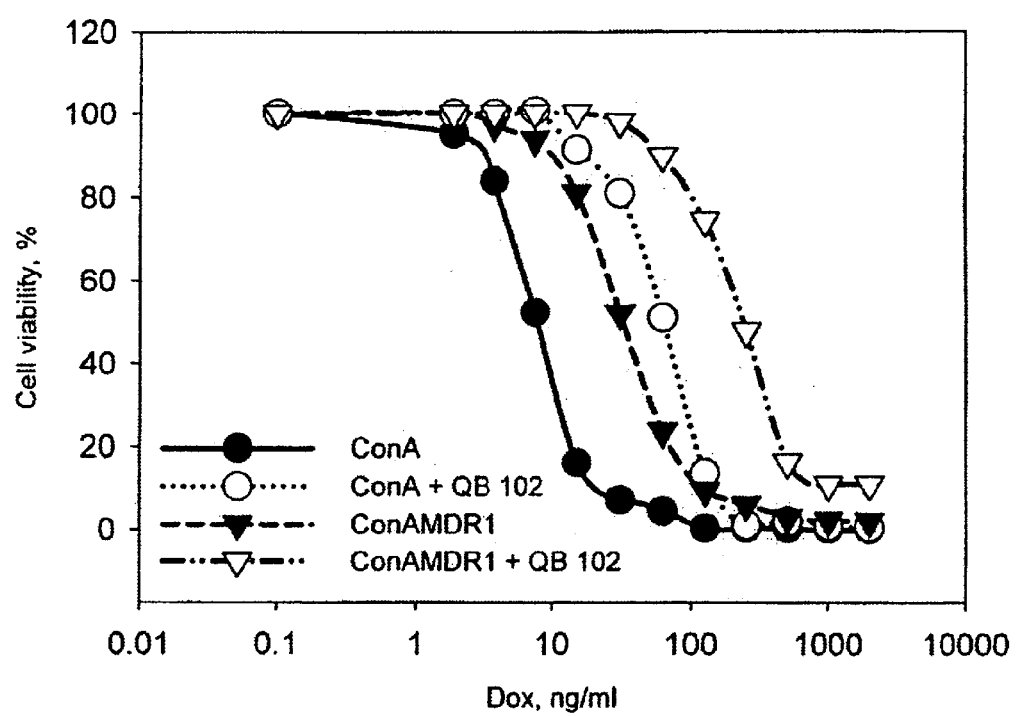
FIG. 10 contains plots of cell viability (%) vs. doxorubicin concentration (ng/ml) to test to determine doxorubicin resistance of mouse cells expressing human P-gp.

It also has been shown that Compound 102 increases doxorubicin resistance of mouse cells expressing human P-pg. In particular, the modulating effect of the identified compounds in MDR KB-8-5-11 cells has been demonstrated. These cells are known to overexpress P-gp as result of MDR1 gene amplification. To completely eliminate possibility that some other ABC type transporter expressed in KB-8-5-11 cells might be responsible for this phenomenon, mouse fibroblasts, line ConA, permanently expressing human P-gp as a result of transfection with MDR1 cDNA-expressing plasmid LNL6 were used. As previously shown with KB-8-5-11, Compound 102 increased resistance to doxorubicin (FIG. 10) and decreased resistance to vinblastine (data not shown). This protective effect was completely eliminated by treatment with 1 μM verapamil. FIG. 10 shows that an identified compound protects mouse cells that originally express very low levels of endogenous P-gp, but were made P-gp-positive by transfection with the construct expressing human MDR1 gene under Mo-MuLV LTR promoter. This result provides proof that Compound 102 targets P-gp.

To show that Compound 102 acts as a general activator of P-gp function, its effects on cell sensitivity to various P-gp substrates was tested. Compound 102 has different effect on cell sensitivity to different P-gp substrates (Table 2), which, according to this criterion, can be divided in three groups. The first group includes drugs that become less toxic in the presence of Compound 102. Besides Adr and Rho123, the group also contains daunorubicin and etoposide, although the effect of Compound 102 on cytotoxicity of the latter drug was less pronounced. The second group consists of drugs that become more potent in combination with Compound 102, e.g., taxol, vincristine, vinblastine, gramicidin D, and Hoechst 33342. Finally, the third group contains P-gp substrates that do not change their cytotoxicity in the presence of Compound 102 (e.g., actinomycin D, colcemid, cytochalasin D and puromycin). FIG. 2b illustrates the influence of Compound 102 on cell sensitivity compared to representatives of each of these three groups. Importantly, Compound 102 did not affect cell sensitivity to any of the non-P-gp substrates tested (see Table 2).

The differential effect of Compound 102 on cell sensitivity to different P-gp substrates suggested that Compound 102 acts by modulating P-gp activity, making it more effective against some substrates and less effective against other substrates. To test this possibility, the effect on Compound 102 on the P-gp-mediated efflux of taxol, the P-gp substrate belonging to the second group of drugs becoming more potent in the presence of Compound 102, was tested. Consistent with the drug sensitivity data, Compound 102 suppressed P-gp-mediated efflux of taxol by KB-8-5-11 cells, acting as a P-gp inhibitor for this drug (FIGS. 4 and 5). These observations indicate that Compound 102 should be defined as a modulator rather than a general activator of P-gp that acts by changing relative substrate specificity of the transporter.

In addition, it was found that Compound 102 modulates activity of P-gp, but does not cause an affect on another ABC transporter, MRP1. To determine transporter specificity of the identified compounds, the compounds were tested on cells differing in the type of multidrug transporter expressed: KB-8-5-11 cells, (expressing P-gp), SW1753-A120 cells (expressing MRP1), and KB-3-1 (expressing neither of the above transporters and highly sensitive to drugs that are P-gp or MRP1 substrates). FIGS. 12–17 demonstrate that Compound 102 increases doxorubicin resistance and decreases vinblastine resistance of P-gp-positive cells. Compound 102 has no effect on the cells that express MRP1, but do not express P-gp.

Compound 103 modulates drug resistance independently of the expression of P-gp and MRP1. In contrast to Compound 102, Compound 103 increases doxorubicin resistance and vinblastine sensitivity of P-gp-negative, MRP1 positive cells (FIGS. 12–17). This is not an MRP1-mediated phenomenon because Compound 103 causes a similar effect on P-gp- and MRP1-negative cells KB-3-1. These effects were verapamil sensitive in all cell lines tested (data not shown) indicating that Compound 103 alters cell drug sensitivity by modulating an unidentified ABC transporter.

Figure 12:
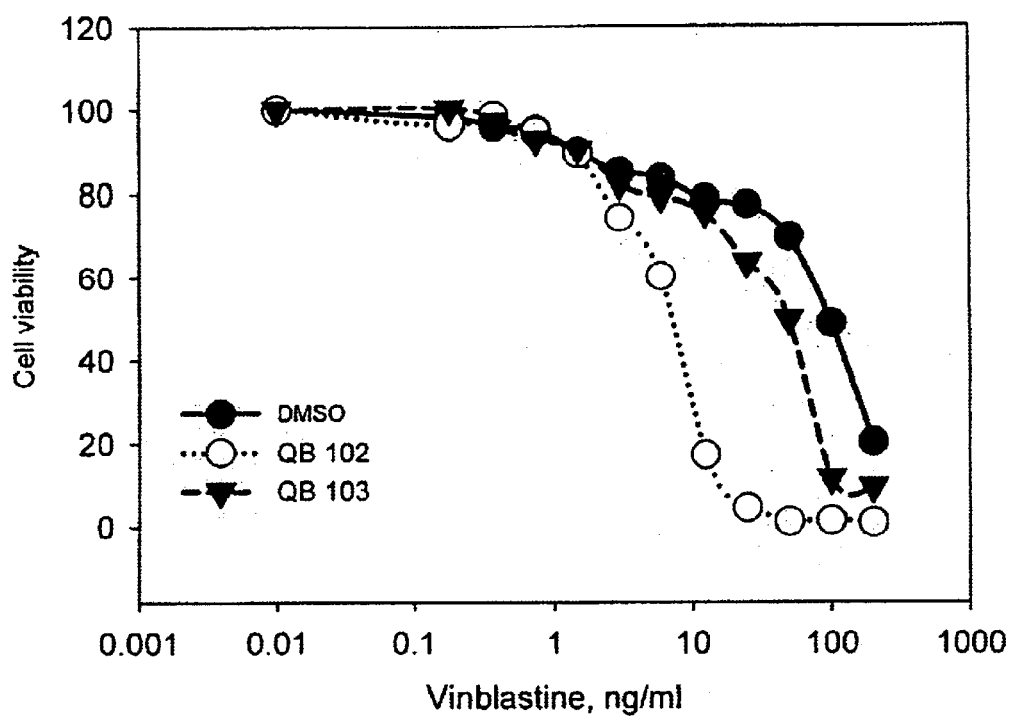
FIGS. 12–14 contain plots of cell viability (5) vs. vinblastine concentration (mg/ml) for tests to show the effect of Compounds 102 and 103 on vinblastine sensitivity for different types of cells.
Figure 13:
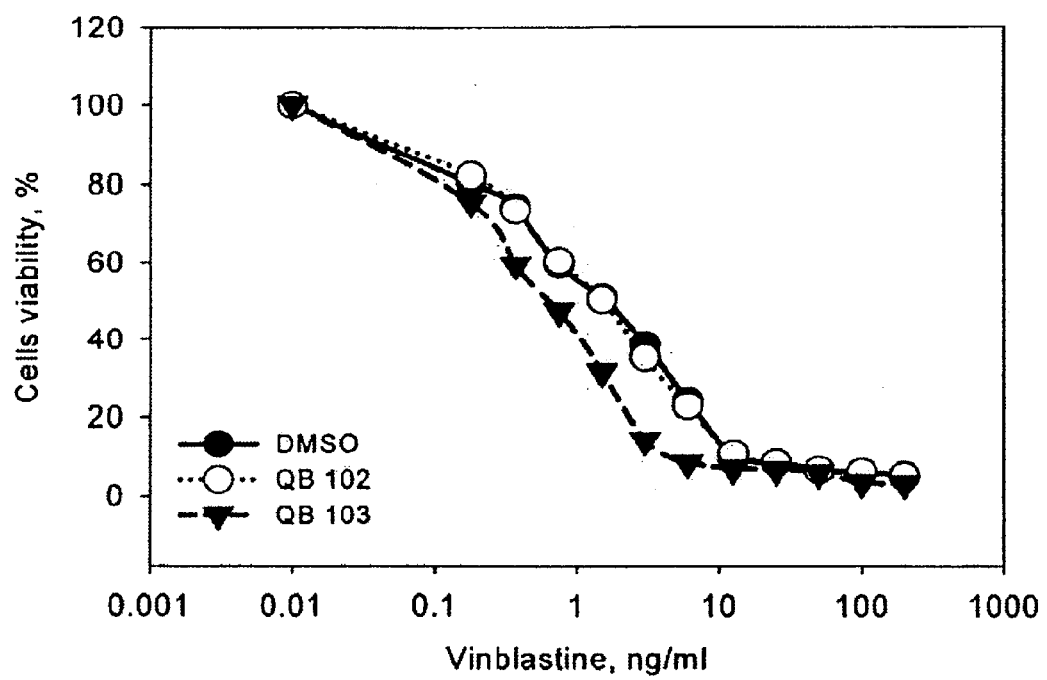
Figure 14:
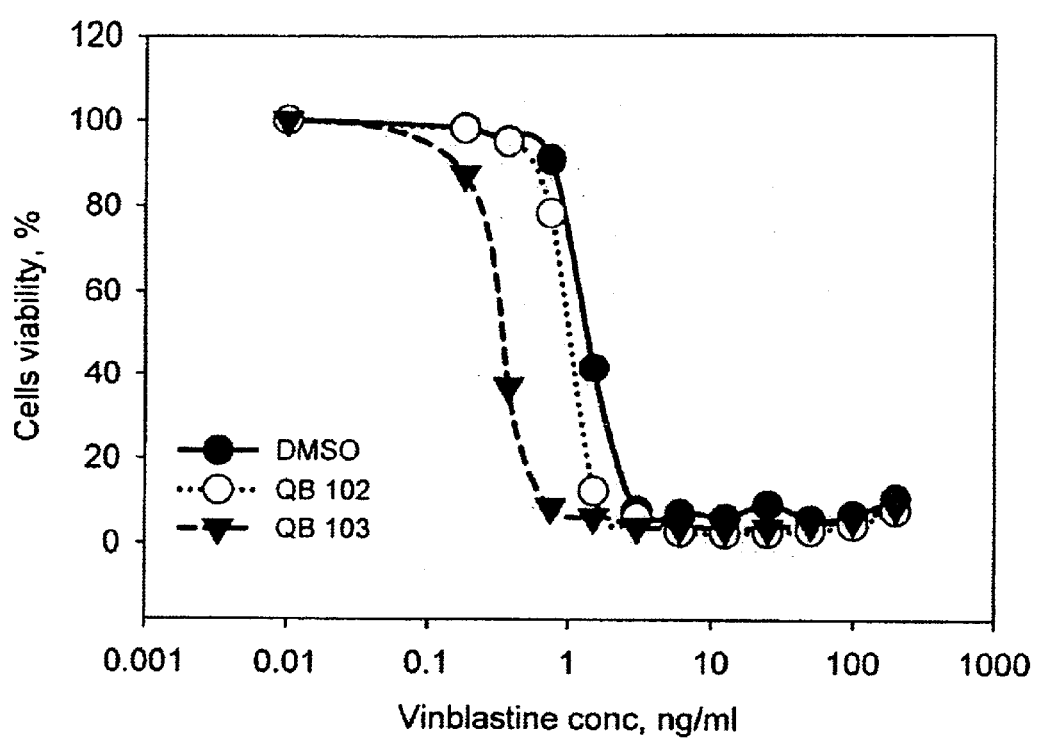

In particular, FIG. 12 shows that Compound 102 sensitizes P-gp-positive cells to vinblastine, and compound 103 has similar but much weaker effect. FIG. 13 shows that Compound 102 does not effect cell sensitivity to vinblastine in the absence of P-gp. Compound 103 has a weak sensitizing effect on cells treated with vinblastine, regardless of whether they express P-gp or MRP1. FIG. 14 shows that Compound 102 does not effect cell sensitivity to vinblastine in the absence of P-gp and MRP1. Compound 103 has weak sensitizing effect on cells treated with vinblastine even in the absence of P-gp and MRP1.

Figure 15:
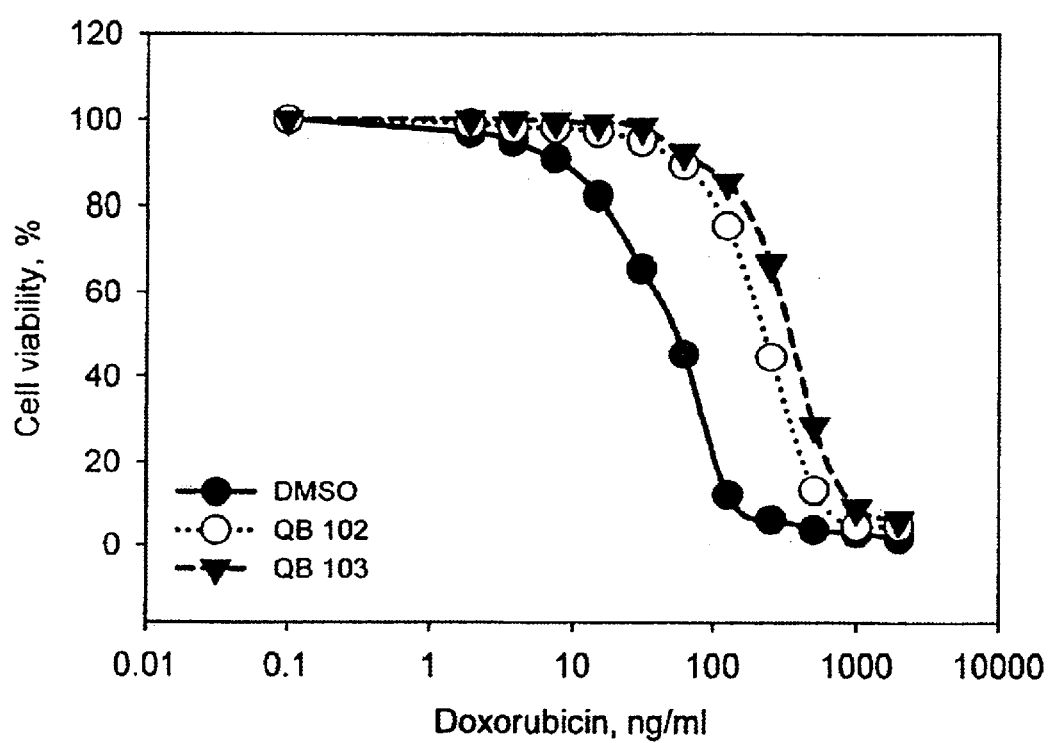
FIGS. 15–17 contain plots of cell viability (%) vs. doxorubicin concentration (ng/ml) for tests to show the effect of Compounds 102 and 103 on doxorubicin sensitivity for different types of cells.
Figure 16:
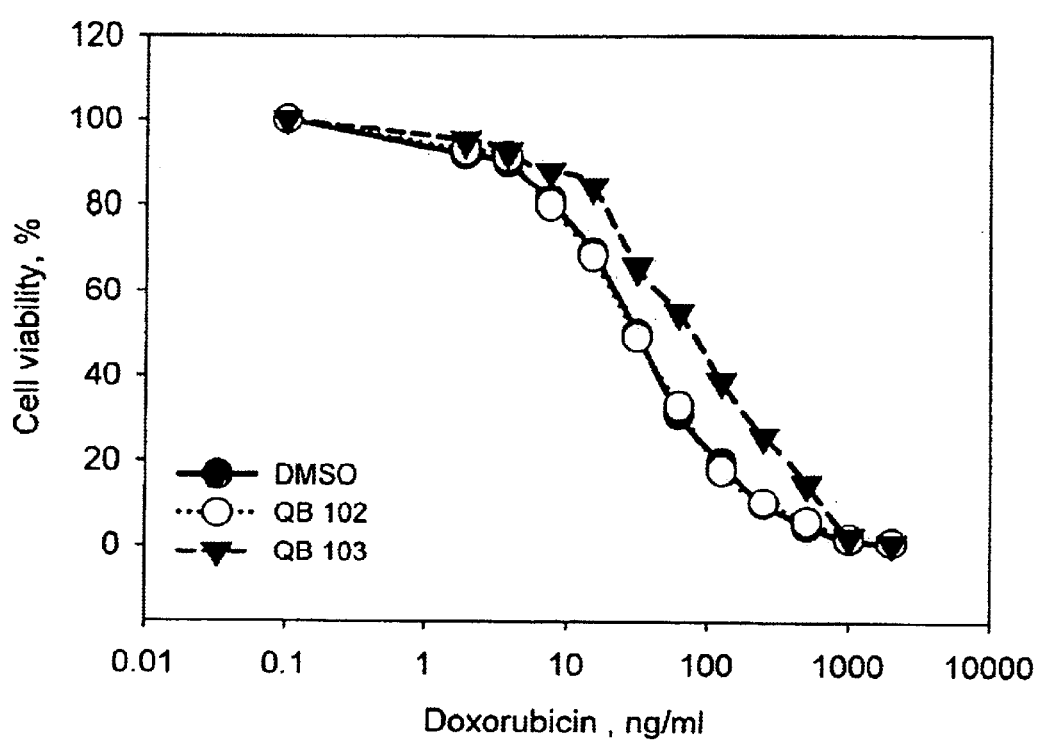
Figure 17:
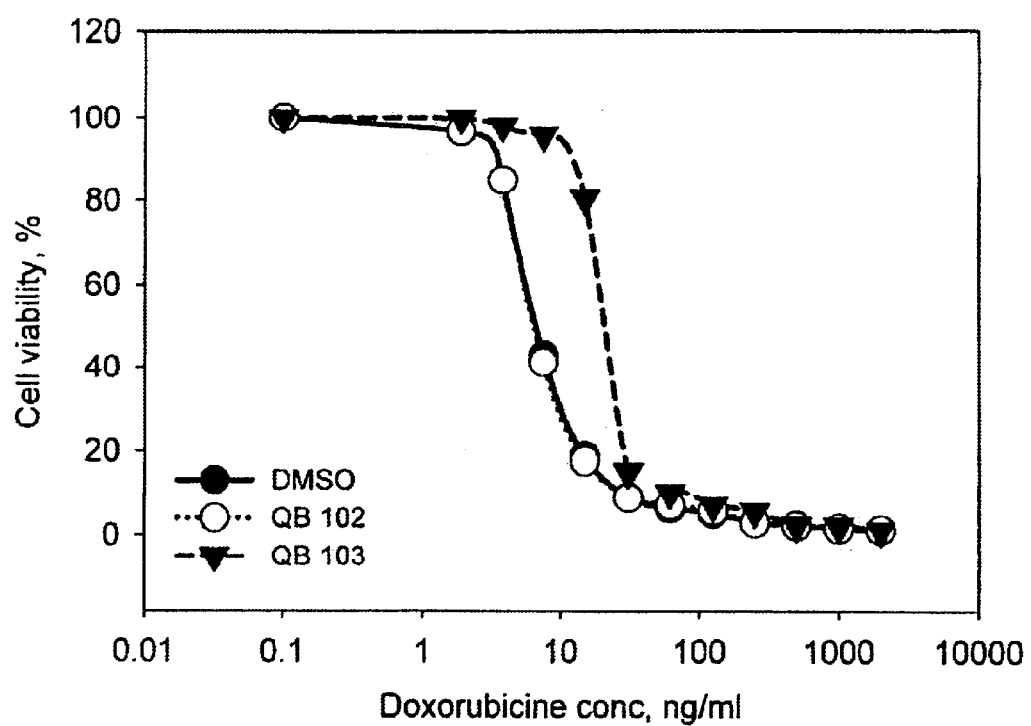

FIG. 15 shows that both Compounds 102 and 103 increase cell sensitivity to doxorubicin in the presence of P-gp. FIG. 16 shows that Compound 102 does not effect cell sensitivity to doxorubicin in the absence of P-gp even if MRP1 is expressed. Compound 103 increases sensitivity of P-gp-negative MRP1-positive cells to doxorubicin. FIG. 17 shows that Compound 103 can increase cell resistance to doxorubicin in the absence of both P-gp and MRP1, presumably by modulating activity of an unidentified transporter that normally does not recognize doxorubicin as a substrate.

Figure 11:
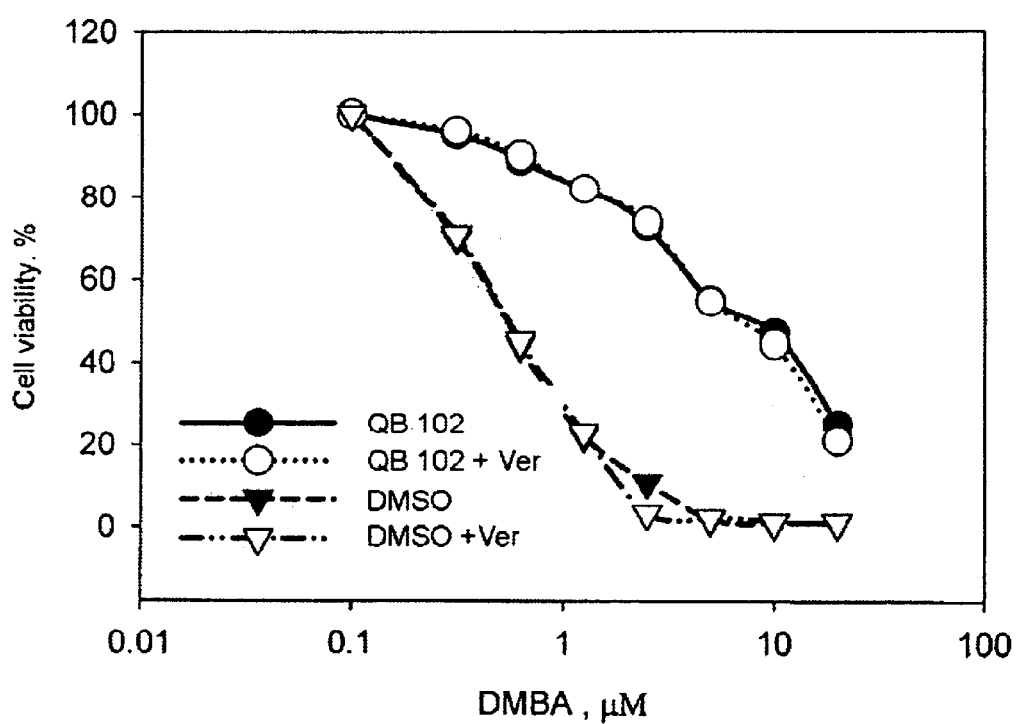
FIG. 11 contains plots of cell viability (%) vs. DMBA concentration ($\mu$M) for tests to show the effect of Compound 102 on the sensitivity of mouse ConA cells to DMBA.

The effect of the identified compounds on DMBA sensitivity of mouse cells also was tested. It has been reported that ABC type transporters (e.g., P-gp) are involved in the efflux of polycyclic aromatic hydrocarbon carcinogens from cells. The effect of the identified compounds on sensitivity of mouse cells to 7,12-dimethylbenz[a]anthracene (DMBA) was determined. Mouse fibroblasts were incubated in 96 well plates for three days in the presence of 10 $\mu$M Compound 102, 1 $\mu$M verapamil, and indicated concentrations of DMBA. FIG. 11 demonstrates that Compound 102 strongly protects cells from cytotoxicity of DMBA ($IC_{50}$ increases from 0.31 to 5 $\mu$M), thus increasing greater than 15 fold the natural level of resistance to this chemical carcinogen. In similar experiments Compounds 11, 13, and 16 also demonstrated a strong protective effect.

P-gp Modulators Vary in Their Relative Effect on Different P-gp Substrates

Figure 8:
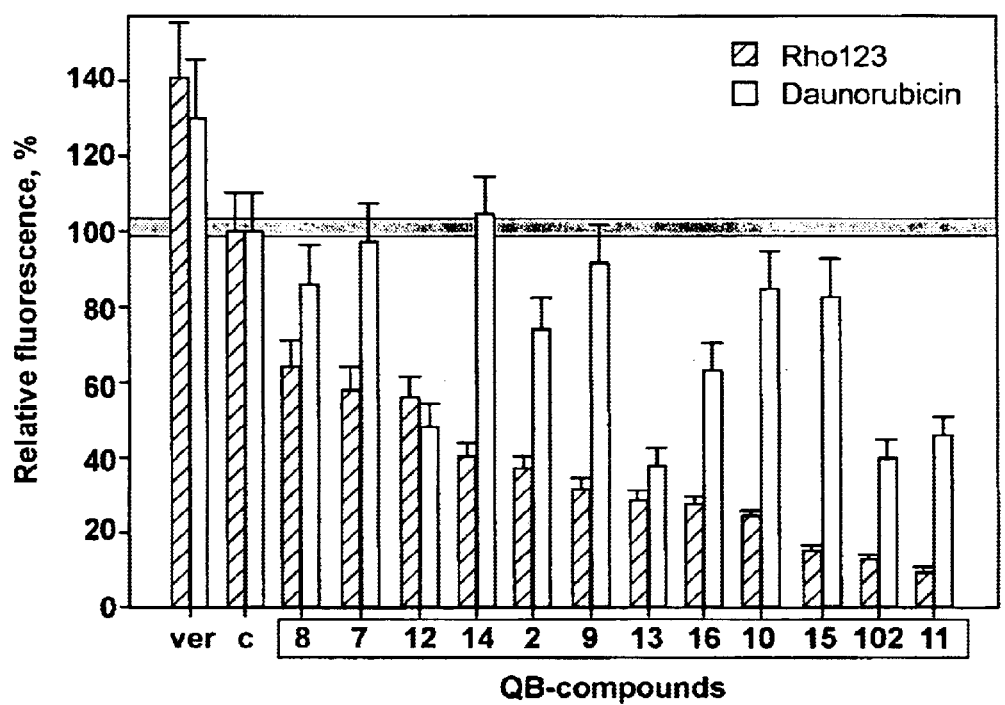
FIG. 8 contains bar graphs of relative fluorescence (%) for tests using Rho123 and daunorubicin showing their effect on various identified compounds.

The effect of other compounds identified for their stimulation of Adr accumulation on cellular uptake of two fluorescent P-gp substrates was tested, i.e., Rho123 and daunorubicin. Daunorubicin was used in these experiments rather than Adr because its brighter fluorescence, thereby facilitating quantitative determination of drug accumulation. All of the compounds stimulated a decrease in accumulation of Rho123 (FIG. 8). Whether the identified compounds had similar effects on the substrate specificity of P-gp was tested by determining their relative effect on the efflux of two P-gp substrates, i.e., Rho123 and daunorubicin.

Figure 9:
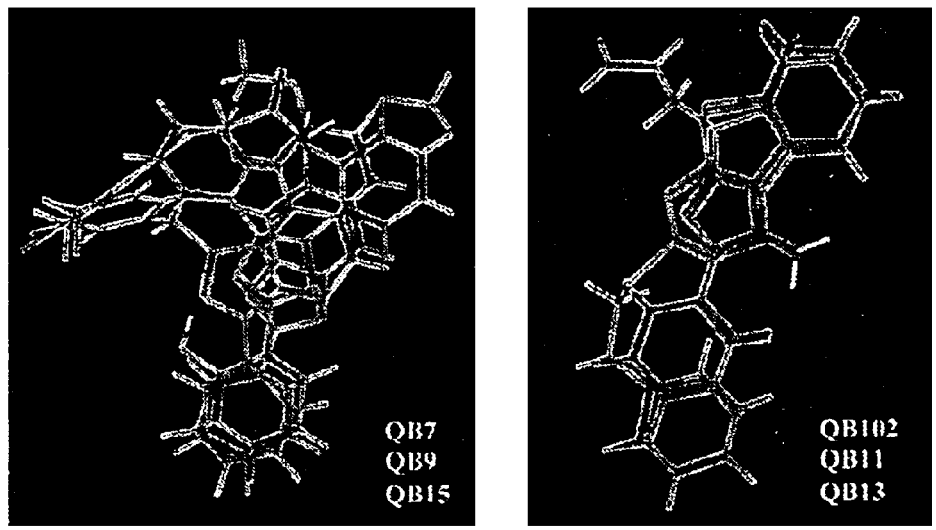
FIG. 9 shows three-dimensional representations of compounds used in methods of the invention.

FIGS. 8 and 9 show differences in relative effects of isolated P-gp modulators on different P-gp substrates correlate to some degree to their structures. FIG. 8 shows a comparison of the effect of each P-gp modulator on efflux of daunorubicin and Rho123. ConA cells were incubated two hours with Rho123 (1M) or daunorubicin (500 ng/ml) in the presence of the identified compounds, and accumulation of the drugs was quantitated by flow cytometry. The compounds are shown in the order of their relative ability to stimulate Rho123 efflux compared to accumulation of the drugs in the absence of the P-gp modulators ("c") or in the presence of verapamil ("ver"). As seen in FIG. 8, the identified compounds significantly differ in their ability to modulate P-gp activity against these two drugs. This observation indicates the possibility of identification of P-gp modulators with targeted activity against certain classes of P-gp substrates. In all cases, the decreased accumulation correlated with stimulation of P-gp dependent verapamil-sensitive drug efflux.

The identified compounds fell into different categories according to their effect of daunorubicin accumulation. Some of them behaved similarly to Compound 102 (i.e., Compounds 11 and 13) causing a strong effect on Rho123 and a two to four times less pronounced effect on daunorubicin. Compounds of another group (i.e., Compounds 2, 3, 7, 8, 9, 10, 15, and 16) were relatively effective in stimulating Rho123 efflux, but had a weak influence on daunorubicin accumulation. Two compounds from this group (Compound 4 and Compound 14) had no effect on daunorubicin accumulation. Finally, one compound (Compound 12) was more effective in stimulating P-gp-mediated efflux of daunorubicin than Rho123.

Next, effect of compound treatment on cell resistance to daunorubicin was tested. As in the case of Compound 102, drug accumulation data correlated well with the results of drug sensitivity assays. All compounds that demonstrated strong stimulatory effect on Rho123 efflux increased cell sensitivity to taxol and vinblastine.

Structural relationships among the different compounds were examined both by the evaluation of two-dimensional similarity and by molecular modeling. In general, the set of identified compounds was found to be structurally diverse as evidenced by a relatively low structural likeness, i.e., in terms of Tanimoto metrics, only Compound 15 and Compound 9 had over 75% similarity. The latter compound also showed a 61% similarity quotient with Compound 7, while all other two-dimensional structure comparisons gave lower similarity rates.

Alignment of the three-dimensional models of Compounds 7, 9, and 15 showed two shared structural motifs: similarly placed hydrogen bond acceptors and six member aromatic rings, suggesting that these particular compounds may be addressing some common pGP binding regions (FIG. 3b). Interestingly, the above compounds are members of the group that stimulates Rho123 efflux with a relatively weak influence on daunorubicin accumulation. In parallel, the three-dimensional alignment of Compound 102 with Compound 11 and Compound 13 showed good superposition (FIG. 9), again in accordance with their biological activity. FIG. 9 shows flexible alignments of three-dimensional models of the indicated compounds. Light blue regions symbolize hydrogen bond acceptors.

The identification of P-gp modulators was a surprising and unexpected discovery made in connection with screening of a chemical library for p53 inhibitors in which Adr was used as a DNA-damaging agent inducing p53. Several compounds previously have been identified that target the activity of P-gp, the vast majority of which act as P-gp inhibitors (5), sensitizing cells to a variety of P-gp substrates. However, in accordance with the present invention, a class of structurally divergent compounds capable of protecting cells from a drug by stimulating the P-gp-mediated efflux has been identified. The compounds were found to act not as general stimulators of P-gp activity, but rather as P-gp modulators making this transporter much more active against some substrates and inactive against other substrates.

"Retargeting" P-gp by the identified compounds causes a dramatic change of the MDR phenotype making P-gp-expressing cells more resistant to some drugs at the cost of losing resistance to others. These findings indicate that cell resistance to toxic compounds can be dramatically increased by modulating the substrate specificity of multidrug transporters, thereby broadening the approaches to rational control over the MDR phenotype by small molecules.

Prior publications suggest that P-gp substrate specificity can be modulated by natural flavonoid polyphenols. Quercetin was reported to act as a stimulator P-gp-mediated efflux of 7,12-dimethylbenz(a)anthracene (21) and Adr (22). However, other investigators disclosed an opposite effect of quercetin at least on Adr efflux and resistance (23), and a systematic study of flavonoid derivatives were consistent with the latter results (24). Other investigators found that the P-gp substrates prazosin and progesterone modulate efflux of other substrates in an in vitro system (25), suggesting that these compounds can be modulators of MDR phenotype. Although a weak effect of prazosin and progesterone on P-gp-mediated Rho123 efflux in vivo was confirmed, these compounds did not cause detectable changes in cell cross resistance to P-gp substrates tested, i.e., Adr, vincristine, vinblastine, taxol, actinomycin D, and colcemide. Thus, although prazosin and progesterone formally belong to the category of P-gp modulators, these compounds are too weak to be used as modulators of MDR.

There are at least three possible hypotheses with respect to how P-gp modulators work. First, it can be theorized that they cause a conformational change in P-gp itself, thus acting through the same mechanism that determines alterations of the substrate specificity of some P-gp mutants (12–15). An attempt to test this possibility by using FACS analysis with conformation sensitive antibodies UIC2 (19) was made but failed to detect any changes in the reactivity of P-gp in the presence of the isolated modulators. Alternatively, the compounds may alter the physicochemical properties of the drug recognition pockets in the protein without changing conformation of the transporter. There also is a possibility that the modulators do not interact with P-gp directly, but modulate its function by altering the properties of plasma membrane or factors contributing to the activity of the transporter.

Comparison of biological effects of the identified P-gp modulators showed that they differ in their relative effect on the substrate specificity of P-gp, modifying the MDR phenotype in a way specific for each compound. If they act through changing conformation of P-gp, this would mean high conformational plasticity of this protein that could accept multiple different conformations still keeping its basic drug efflux function. Another assumption that follows from this observation is that P-gp activity can be finely "tuned" by the appropriate modulators to make it more effective against the desired toxins.

In addition, based on the number of P-gp modulators in the chemical library, similar selection performed on another cell-based readout system expressing non-P-gp ABC transporter (MRP, LRP, BCRP, etc.) is expected to result in the identification of appropriate modulators.

To date, P-gp and other ABC transporters have been viewed mainly as targets for suppression considering their role in multidrug resistance of cancer. The present invention provides additional practical applications of ABC transporters that stem from their natural function, i.e., involvement in the protection of cells and tissues from broad variety of cytotoxic compounds. The modulators of substrate specificity of the transporters, making them more active against certain classes of drugs, can be used to facilitate chemoprotection under the condition of acute or chronic poisoning with toxins or drugs. Selection of targeted modulators opens the possibility of development of detoxifying agents specific against certain classes of toxins.

ABC transporters are known to be involved in blood-brain barrier and in placental barrier, thus defending brain tissue and fetuses against toxicity of a variety of toxic factors. Low efficiency of these defense systems against particular substrates can limit the application of high doses of otherwise useful drugs (i.e., cyclosporin A or ivermectin, (7)). Modulators of P-gp and other transporters could increase tolerable doses of such drugs by increasing the effectiveness of these natural barriers. Moreover, the use of highly specific targeted modulators of ABC transporters can be beneficial for selective delivery of useful drugs through blood-brain and placental barriers without general affection of these defense systems against other factors.

As set forth below, administration of a multidrug transporter modulator to a mammal has several potential benefits, including, for example, rescuing cells from acute or chronic toxins, or improving treatment using a chemotherapeutic or antibiotic drug.

The multidrug transporter modulators can be therapeutically administered as the neat chemical, but it is preferable to administer the modulators as a pharmaceutical composition or formulation. Accordingly, the present invention further provides for pharmaceutical formulations comprising, for example, a multidrug transporter modulator, or pharmaceutically acceptable salt or prodrug thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

The amount of a multidrug transporter modulator required for use in therapy varies with the nature of the condition being treated, the length of time modulation is desired, and the age and the condition of the patient, and is ultimately determined by the attendant physician. In general, however, doses employed for adult human treatment typically are in the range of 0.001 mg/kg to about 200 mg/kg per day. A preferred dose is about 1 µg/kg to about 100 µg/kg per day. The desired dose can be conveniently administered in a single dose, or as multiple doses administered at appropriate intervals, for example as two, three, four or more subdoses per day. Multiple doses often are desired, or required, because modulation of multidrug transporter activity can be temporary.

A "therapeutically effective" dose refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a range of dosage for use in humans. The dosage of such compounds preferably lies within a range of circulating concentrations that include the $ED_{50}$ with little or no toxicity. The dosage can vary within this range depending upon the dosage form employed, and the route of administration utilized.

Formulations of the present invention can be administered in a standard manner, such as orally, parenterally, sublingually, transdermally, rectally, transmucosally, topically, via inhalation, or via buccal administration. Parenteral administration includes, but is not limited to, intravenous, intraarterial, intraperitoneal, subcutaneous, intramuscular, intrathecal, and intraarticular.

For veterinary use, multidrug transporter modulator, or a nontoxic salt or prodrug thereof, is administered as a suitably acceptable formulation in accordance with normal veterinary practice. The veterinarian can readily determine the dosing regimen and route of administration that is most appropriate for a particular animal.

A pharmaceutical composition containing a multidrug transporter modulator can be in the form of tablets or lozenges formulated in conventional manner. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline cellulose, maize-starch, calcium phosphate, or sorbitol), lubricants (for example, magnesium stearate, stearic acid, talc, polyethylene glycol, or silica), disintegrants (for example, potato starch or sodium starch glycollate), or wetting agents (for example, sodium lauryl sulfate). The tablets can be coated according to methods well known in the art.

Alternatively, a multidrug transporter modulator can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, like suspending agents, such as sorbitol syrup, methyl cellulose, glucose/sugar syrup, gelatin, hydroxyethylcellulose, carboxymethyl cellulose, aluminum stearate gel, and hydrogenated edible fats; emulsifying agents, such as lecithin, sorbitan mono-oleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical transdermal formulations comprise conventional aqueous or nonaqueous vehicles, such as creams, ointments, lotions, and pastes, or are in the form of a medicated plaster, patch, or membrane.

Additionally, compositions of the present invention can be formulated for parenteral administration by injection or continuous infusion. It is envisioned that injection or continuous infusion is the preferred method of administration. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for reconstitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (as an emulsion in an acceptable oil, for example), ion exchange resins, or as sparingly soluble derivatives (as a sparingly soluble salt, for example).

A multidrug transporter modulator also can be used in combination with other therapeutic agents which can be useful in the treatment of cancer and other conditions or disease states. The invention thus provides, in another aspect, a combination of a therapeutic, multidrug transporter modulator together with a second therapeutically active agent.

A multidrug transporter modulator, can be used in the preparation of a medicament for coadministration with the second therapeutically active agent in treatment of conditions where modulation of multidrug transporter activity is beneficial. In addition, a multidrug transporter modulator can be used in the preparation of a medicament for use as adjunctive therapy with a second therapeutically active compound to treat such conditions. Appropriate doses of known second therapeutic agents for use in combination with a multidrug transporter modulator are readily appreciated by those skilled in the art.

For example, a therapeutic, multidrug transporter modulator can be used in combination with a cancer therapy, such as chemotherapy. In particular, a multidrug transporter modulator can be used in conjunction with chemotherapeutic drugs, such as cis-platin, doxorubicin, Vinca alkaloids, taxol, cyclophosphamide, ifosphamide, chlorambucil, busulfan, mechlorethamine, mitomycin, dacarbazine, carboplatin, thiotepa, daunorubicin, idarubicin, mitoxanthrone, bleomycin, esperamicin $A_1$, plicamycin, carmustine, lomustine, tauromustine, streptozocin, melphalan, dactinomycin, topotecan, adriamycin, camptothecin, interferon (alpha, beta, gamma), interleukin 2, irinotecan, docetaxel, and procarbazine, and therapeutically effective analogs, prodrugs, and derivatives thereof, for example. A multidrug transporter modulator also can be used in combination with drugs used to treat a condition caused by a pathogen, virus, parasite, or other microbiological vector, for example, an antiinfective, like an antibiotic.

Additional chemotherapeutic agents that can be used with a present multidrug transporter modulator include, but are not limited to, alkylating agents, antimetabolites, hormones and antagonists thereof, radioisotopes, antibodies, as well as natural products, and combinations thereof. For example, a multidrug transporter modulator of the present invention can be administered with antibiotics, such as doxorubicin and other anthracycline analogs, nitrogen mustards, such as cyclophosphamide, pyrimidine analogs such as 5-fluorouracil, cisplatin, hydroxyurea, taxol and its natural and synthetic derivatives, and the like. As another example, the modulator can be administered in conjunction with leuprolide or goserelin (synthetic peptide analogs of LH-RH). Examples of chemotherapeutic agents useful for the method of the present invention are listed in the following table.

| | | |
|---|---|---|
| Alkylating agents | Epipodophylotoxins | Hormones and antagonists |
| Nitrogen mustards | etoposide | Adrenocorticosteroids/ |
| mechlorethamine | teniposide | antagonists |
| cyclophosphamide | Antibiotics | prednisone and equiv- |
| ifosfamide | actimomycin D | alents |
| melphalan | daunomycin (rubido- | dexamethasone |
| chlorambucil | mycin) | ainoglutethimide |
| Nitrosoureas | doxorubicin (adria- | Progestins |
| carmustine (BCNU) | mycin) | hydroxyprogesterone |
| lomustine (CCNU) | mitoxantroneidarubicin | caproate |
| semustine (methyl-CCNU) | bleomycinsplicamycin | medroxyprogesterone |
| Ethylenimine/Methyl- | (mithramycin) | acetate |
| melamine | mitomycinC | megestrol acetate |
| thriethylenemelamine | dactinomycin | Estrogens |
| (TEM) | Enzymes | diethylstilbestrol |
| triethylene | L-asparaginase | ethynyl estradiol/ |
| thiophosphoramide | Biological response | equivalents |
| (thiotepa) | modifiers | Antiestrogen |
| hexamethylmelamine | interferon-alpha | tamoxifen |
| (HMM, altretamine) | IL-2 | Androgens |
| Alkyl sulfonates | G-CSF | testosterone propionate |
| busulfan | GM-CSF | fluoxymesterone/equiv- |
| Triazines | Differentiation Agents | alents |
| dacarbazine (DTIC) | retinoic acid deriva- | Antiandrogens |
| Antimetabolites | tives | flutamide |
| Folic Acid analogs | Radiosensitizers | gonadotropin-releasing |
| methotrexate | metronidazole | hormone analogs |
| trimetrexate | misonidazole | leuprolide |
| Pyrimidine analogs | desmethylmisonidazole | Nonsteroidal |
| 5-fluorouracil | pimonidazole | antiandrogens |
| fluorodeoxyuridine | etanidazole | flutamide |
| gemcitabine | nimorazole | Photosensitizers |
| cytosine arabinoside | RSU 1069 | hematoporphyrin |
| (AraC, cytarabine) | EO9 | derivatives |
| 5-azacytidine | RB 6145 | Photofrin ® |
| 2,2'-difluorodeoxy- | SR4233 | benzoporphyrin |
| cytidine | nicotinamide | derivatives |
| Purine analogs | 5-bromodeozyuridine | Npe6 |
| 6-mercaptopurine | 5-iododeoxyuridine | tin etioporphyrin |
| 6-thioguanine | bromodeoxycytidine | (SnET2) |
| azathioprine | Miscellaneous agents | pheoboride-a |
| 2'-deoxycoformycin | Platinium coordination | bacteriochlorophyll-a |
| (pentostatin) | complexes | naphthalocyanines |
| erythrohydroxynonyl- | cisplatin | phthalocyanines |
| adenine (EHNA) | carboplatin | zinc |
| fludarabine phosphate | Anthracenedione | phthalocyanines |
| 2-chlorodeoxyadenosine | mitoxantrone | |
| (cladribine, 2-CdA) | Substituted urea | |
| Type I Topoisomerase | hydroxyurea | |
| Inhibitors | Methylhydrazine deriva- | |
| camptothecin | tives | |
| topotecan | N-methylhydrazine (MIH) | |
| irinotecan | procarbazine | |
| Natural products | Adrenocortical suppres- | |
| Antimitotic drugs | sant | |
| paclitaxel | mitotane (o,p'-DDD) | |
| Vinca alkaloids | ainoglutethimide | |
| vinblastine (VLB) | Cytokines | |
| vincristine | interferon (α, β, γ) | |
| vinorelbine | interleukin-2 | |
| Taxotere ® (docetaxel) | | |
| estramustine | | |
| estramustine phosphate | | |

The multidrug transporter modulator also can be used in conjunction with an antiinfective agent. An antiinfective agent is a drug used to treat an individual suffering from a disease or condition caused by a bacteria, virus, parasite, or other microbiological or microscopic vector.

Antibiotic agents that can be used include, but are not limited to, sulfonamides, such as sulfacetamide sodium, sulfacycline, sulfadiazine, sulfabenzamide, sulfadoxine, sulfamerazine, sulfamethazine, sulfmethizole, sulfamethoxazole, sulfanilamide, sulfapyridine, sulfasalazine, and sulfisoxazole; a penicillin, such as penicillin G, penicillin V, cloxacillin, dicloxacillin, methicillin, nafcillin, oxacillin, amoxacillin, ampicillin, bacampicillin, cyclacillin, carbenicillin, indanyl-carbenicillin, melocillin, piperacillin, and ticarcillin; a cephalosporin, such as cefadroxil, cefazolin, cephalexin, cephalothin, cephapirin, cephradine, cefaclor, cefamandole, cefmetazole, cefonicid, ceforanid, cefotetan, cefoxitin, cefpodoxime, cefprozil, cefuroxine, loracef, cefixime, cefoperazone, cefataxime, ceftazidime, ceftizoxime, ceftriaxone, or moxalactam; an aminoglycoside, such as amikacin sulfate, gentamicin sulfate, kanamycin sulfate, neomycin sulfate, nefilmican sulfate, streptomycin sulfate, and tobramycin; a macrolide, such as azithromycin, clarithromycin, erythromycin, spiramycin, and troleandomycin; a polypeptide, such as bacitracin, capreomycin sulfate, colistimethate sodium, colistin sulfate, polymyxin B sulfate, and vanomycin; a tetracycline, such as chlorotetra-cycline hydrochloride, demeclocycline hydrochloride, doxycycline, minocycline, oxytetracycline, and tetracycline; a fluoroquinolone, such as ciprofloxacin hydrochloride, enoxacin, lomefloxacin hydrochloride, norfloxacin, and ofloxacin; and miscellaneous antibiotics, such as chloramphenicol, clindamycin, cycloserine, fusidate sodium, ritampin, spectinomycin hydrochloride, cinoxacin, clofazimine, dapsone, ethambutal hydrochloride, isoniazid, nitro-furantoin, pyrazinamide, rifabutin, and trimethoprim. Addition classes of antibacterials include antimalarial and antifungal drugs. Antiviral drugs, such as acyclovir, cytarabine, didanosine, fos-carnet, genciclovir, idoxuridine, an interferon, methisazone, rifampin, suramin, vidarabine, zalcitabine, and zidovudine, also can be used. Other antiinfective agents known to persons skilled in the art, and salts, derivatives, and prodrugs of antiinfective agents also can be used.

The combination referred to above can be presented for use in the form of a single pharmaceutical formulation, and, thus, pharmaceutical compositions comprising a combination as defined above together with a pharmaceutically acceptable diluent or carrier comprise a further aspect of the invention.

The individual components of such a combination referred to above, therefore, can be administered either sequentially or simultaneously from the same or separate pharmaceutical formulations. As is the case for the multidrug transporter modulator, a second therapeutic agent can be administered by any suitable route, for example, by oral, buccal, inhalation, sublingual, rectal, vaginal, transurethral, nasal, topical, percutaneous (i.e., transdermal), or parenteral (including intravenous, intramuscular, subcutaneous, and intracoronary) administration.

In some embodiments, a multidrug transporter modulator, and the second therapeutic agent are administered by the same route, either from the same or from different pharmaceutical compositions. However, in other embodiments, using the same route of administration for the therapeutic multidrug transporter modulator and the second therapeutic agent either is impossible or is not preferred. Persons skilled in the art are aware of the best modes of administration for each therapeutic agent, either alone or in a combination.

Obviously, many modifications and variations of the invention as hereinbefore set forth can be made without departing from the spirit and scope thereof and, therefore, only such limitations should be imposed as are indicated by the appended claims.

Appendix A

1. P. Borst, *Seminars in Cancer Biology*, 8, pp. 131–134 (1997).
2. J. Konig et al., *BBA*, 1461, pp. 377–394 (1999).
3. M. M. Gottesman et al., *Annu. Rev. Biochem.*, 62, pp. 385–427 (1993).
4. B. Tan et al., *Curr Opin Oncol*, 125, pp. 50–58 (2000).
5. B. Sarkadi et al., *Seminars in Cancer Biology*, 8, pp. 171–182 (1997).
6. A. Schinkel, *Seminars in Cancer Biology*, 8, pp. 161–170 (1997).
7. A. H. Schinkel et al., *Cell*, 77, pp. 491–502 (1994).
8. A. H. Schinkel et al., *Proc. Natl. Acad. Sci. USA*, 94, 4028–33 (1997).
9. A. Lorico et al., *Cancer Res.*, 57, pp. 5238–42 (1997).
10. D. F. Robbiani et al., *Cell*, 103, pp. 757–768 (2000).
11. J. J. Smit et al., *Cell*, 75, pp. 451–62 (1993).
12. P. G. Komarov et al., *Science*, 285, pp. 1733–1737 (1999).
13. K. H. Choi et al., *Cell*, 53, pp. 519–529 (1988).
14. P. Gros et al., *Proc. Natl. Acad. Sci. USA*, 88, pp. 7289–7293 (1991).
15. S. Kajiji et al., *Biochemistry*, 32, pp. 4185–4194 (1993).
16. A. R. Safa et al., *Proc. Natl. Acad. Sci. USA*, 87, pp. 7225–7229 (1990).
17. C. A. Hrycyna et al., *Methods Enzymol.*, 292, pp. 456–473 (1998).
18. E. B. Mechetner et al., *Proc Natl Acad Sci USA*, 94, pp. 12908–13 (1997).
19. R. S. Gupta, *Biochem. Biophys. Res. Commun.*, 153, pp. 598–605 (1988).
20. S. Akiyama et al., *Somat. Cell. Mol. Genet.*, 11, pp. 117–26 (1985),
21. J. M. Phang et al., *Cancer Res.*, 53, pp. 5977–5981 (1993).
22. J. M. Critchfieod et al., *Biochem. Pharmacol.*, 48, pp. 1437–1445 (1994).
23. G. Scambia et al., *Cancer Chemother. Pharmacol.*, 34, pp. 459–464 (1994).
24. J. Ferte et al., *J. Med. Chem.*, 42, pp. 478–489 (1999).
25. A. B. Shapiro et al., *Eur J Biochem*, 259, pp. 841–850 (1999).

What is claimed is:

1. A method of modulating an efflux capability of an ABC transporter of a cell or tissue comprising contacting the cell or tissue with a compound that promotes or inhibits efflux of a substrate via the ABC transporter, wherein activity of the ABC transporter through gene expression is unaffected, wherein the compound is selected from the group consisting of 1-carbazol-9-yl-3-(3,5-dimethylpyrazol-1-yl)-propan-2-ol, 2-(4-chloro-3,5-dimethylphenoxy)-N-(2-phenyl-2H-benzo-triazol-5-yl)-acetamide, N-[2-(4-chlorophenyl)acetyl]-N'-(4,7-dimethylguinazolin-2-yl)-guanidine, 1-benzyl-7,8-dimethoxy-3-phenyl-3H-pyrazolo[3,4-c]iso-quinoline, N-(3-benzooxazol-2-yl-4-hydroxyphenyl)-2-p-tolyloxy-acetamide, 8-allyl-2-phenyl-8H-1,3a,8-triaza-cyclopenta[a]indene, 3-(4-chlorobenzyl)-5-(2-methoxyphenyl) [1,2,4]-oxadiazole, 2-phenethylsulfanyl-5,6,7,8-tetrahydro-benzo[4,5]-thieno[2,3-d]pyrimidin4-ylamine, (5,12,13-triaza-indeno[1,2-b]anthracen-13-yl)-acetic acid ethyl ester, 2,2'-(1-phenyl-1H-1,2,4-triazole-3,5-diyl)bis-phenol,2-(2-chlorophenyl)-5-(5-methylthiophen2-yl)-[1,3,4]-oxadiazole, 2-p-tolyl-5,6,7,8-tetrahydrobenzo[d]imidazo[2,1-b]-thiazole,

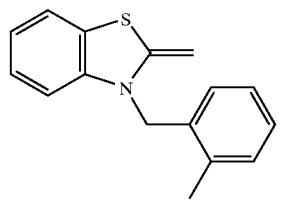

and mixture thereof.

2. The method of claim 1 wherein the ABC transporter is P-glycoprotein.

3. The method of claim 1 wherein the ABC transporter is a member of an MRP family of transporters or LRP.

4. The method of claim 1 wherein the efflux capability is promoted.

5. The method of claim 4 wherein the efflux capability is promoted for a substrate different from a natural substrate of the ABC transporter.

6. The method of claim 1, wherein the efflux capability is inhibited.

7. The method of claim 6, wherein the efflux capability is inhibited for a natural substrate of the ABC transporter.

8. A composition comprising (a) a compound capable of modulating activity of a multidrug transporter, and (b) a pharmaceutically acceptable carrier, wherein the compound is selected from the group consisting of
1-carbazol-9-yl-3-(3,5-dimethylpyrazol-1-yl)-propan-2-ol,
2-(4-chloro-3,5-dimethylphenoxy)-N-(2-phenyl-2H-benzo-triazol-5-yl)-acetamide,
N-[2-(4-chlorophenyl)acetyl]-N'-(4,7-dimethylguin-azolin-2-yl)-guanidine,
1-benzyl-7,8-dimethoxy-3-phenyl-3H-pyrazolo[3,4-c]iso-quinoline,
N-(3-benzooxazol-2-yl-4-hydroxyphenyl)-2-p-tolyloxy-acetamide,
8-allyl-2-phenyl-8H-1,3a,8-triaza-cyclopenta[a]indene,
3-(4-chlorobenzyl)-5-(2-methoxyphenyl) [1,2,4]-oxadiazole,
2-phenethylsulfanyl-5,6,7,8-tetrahydro-benzo[4,5]-thieno[2,3-d]pyrimidin4-ylamine,
(5,12,13-triaza-indeno[1,2-b]anthracen-13-yl)-acetic acid ethyl ester,
2,2'-(1-phenyl-1H-1,2,4-triazole-3,5-diyl)bis-phenol,2-(2-chlorophenyl)-5-(5-methylthiophen2-yl)-[1,3,4]-oxadiazole,
2-p-tolyl-5,6,7,8-tetrahydrobenzo[d]imidazo[2,1-b]-thiazole,

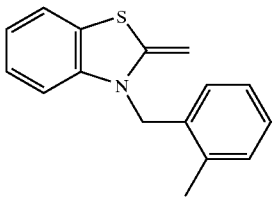

and mixture thereof.

9. The method of claim 1 wherein the compound is selected from the group consisting of
1-benzyl-7,8-dimethoxy-3-phenyl-3H-pyrazolo[3,4-c]-isoquinoline,
8-allyl-2-phenyl-8H-1,3a,8-triaza-cyclopentata[a]-indene,
3-(4-chlorobenzyl)-5-(2-methoxyphenyl) [1,2,4]-oxadiazole,
2-phenethylsulfanyl-5,6,7,8-tetrahydro-benzo[4,5]-thieno[2,3-d]pyrimidin-4-ylamine,
2,2'-(1-phenyl-1H-1,2,4-triazole3,5-diyl)bis-phenyl,
2-p-tolyl-5,6,7,8-tetrahydrobenzo[d]imidazo[2,1-b]-thiazole,

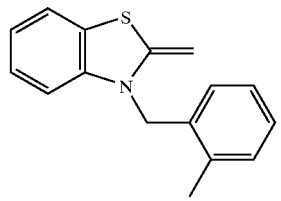

and mixtures thereof.

10. The method of claim 1 wherein the compound is selected from the group consisting of
2-p-tolyl-5,6,7,8-tetrahydrobenzo[d]imidazo[2,1-b]-thiazole,

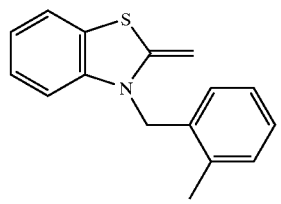

and mixtures thereof.

11. The composition of claim 8 wherein the compound is selected from the group consisting of
1-benzyl-7,8-dimethoxy-3-phenyl-3H-pyrazolo[3,4-c]-isoquinoline,
8-allyl-2-phenyl-8H-1,3a,8-triaza-cyclopenta[a]-indene,
3-(4-chlorobenzyl)-5-(2-methoxyphenyl)[1,2,4]-oxadiazole,
2-phenethylsulfanyl-5,6,7,8-tetrahydro-benzo[4,5]-thieno[2,3-d]pyrimidin-4-ylamine,
2,2'-(1-phenyl-1H1,2,4-triazole-3,5-diyl)bix-phenyl,
2-p-tolyl-5,6,7,8-tetrahydrobenzo[d]imidazo[2,1-b]-thiazole,

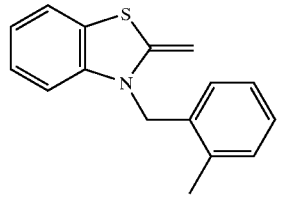

and mixtures thereof.

12. The composition of claim 8 wherein the compound is selected from the group consisting of
2-p-tolyl-5,6,7,8-tetrahydrobenzo[d]imidazo[2,1-b]-thiazole,

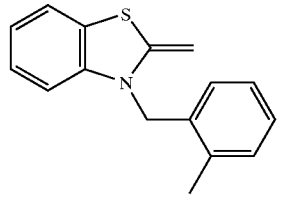

and mixtures thereof.

* * * * *

UNITED STATES PATENT AND TRADEMARK OFFICE
CERTIFICATE OF CORRECTION

PATENT NO.   : 6,861,431 B2
DATED        : March 1, 2005
INVENTOR(S)  : Gudkov et al.

It is certified that error appears in the above-identified patent and that said Letters Patent is hereby corrected as shown below:

Column 24,
Lines 36-37, "dimethylguinazolin" should be -- dimethylquinazolin --.
Line 38, "iso-quinoline" should be -- isoquinoline --.
Line 46, "pyrimidin4" should be -- pyrimidin-4 --.
Line 50, "methylthiophen2" should be -- methylthiophen-2 --.
Line 62, insert a comma after the structure.
Line 64, "is" should be -- is a --.

Column 25,
Line 6 "claim 1," should be -- claim 1 --.
Line 8 "claim 6," should be -- claim 6 --.
Lines 22-23, "dimethylguinazolin" should be -- dimethylquinazolin --.
Line 25, "iso-quinoline" should be -- isoquinoline --.
Line 33, "pyrimidin4" should be -- pyrimidin-4 --.
Line 37, "methylthiophen2" should be -- methylthiophen-2 --.
Line 48, insert a comma after the structure.
Line 50, "mixture" should be -- mixtures --.
Line 57, "cyclopentata" should be -- cyclopenta --.
Lines 59-60, "oxadia zole," should be -- oxadiazole, --.
Line 64, "triazole3" should be -- triazole-3 --.

Column 26,
Lines 10, 25, 49 and 65, insert a comma after the structure.
Line 36, "-lHl," should be -- -1H-1, --.

Signed and Sealed this

Twenty-fifth Day of October, 2005

JON W. DUDAS
*Director of the United States Patent and Trademark Office*